(12) United States Patent
Chodorowski-Kimmes et al.

(10) Patent No.: US 9,504,856 B2
(45) Date of Patent: Nov. 29, 2016

(54) COMPOSITION CONTAINING A COMPOUND CAPABLE OF ESTABLISHING HYDROGEN BONDS, AND COSMETIC TREATMENT PROCESS

(75) Inventors: Sandrine Chodorowski-Kimmes, Senlis (FR); Ivan Rodriguez, Cauffry (FR)

(73) Assignee: L'OREAL, Paris (FR)

( * ) Notice: Subject to any disclaimer, the term of this patent is extended or adjusted under 35 U.S.C. 154(b) by 576 days.

(21) Appl. No.: 12/495,875

(22) Filed: Jul. 1, 2009

(65) Prior Publication Data
US 2010/0028277 A1 Feb. 4, 2010

Related U.S. Application Data

(60) Provisional application No. 61/080,283, filed on Jul. 14, 2008.

(30) Foreign Application Priority Data

Jul. 4, 2008 (FR) ..................................... 08 54556

(51) Int. Cl.
| | |
|---|---|
| *A61K 8/49* | (2006.01) |
| *A61Q 3/02* | (2006.01) |
| *A61Q 1/04* | (2006.01) |
| *A61Q 19/00* | (2006.01) |

(52) U.S. Cl.
CPC ............... *A61Q 3/02* (2013.01); *A61K 8/4953* (2013.01); *A61Q 1/04* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,707,612 A | 1/1998 | Zofchak et al. | |
| 5,972,324 A * | 10/1999 | Zofchak et al. | ........... 424/78.03 |
| 2004/0161394 A1* | 8/2004 | Mougin et al. | ............ 424/70.11 |
| 2007/0264208 A1* | 11/2007 | Mougin et al. | ................. 424/59 |

FOREIGN PATENT DOCUMENTS

| | | |
|---|---|---|
| EP | 1 097 699 | 5/2001 |
| EP | 1 797 867 | 6/2007 |
| WO | WO 2006/118460 | 11/2006 |

* cited by examiner

*Primary Examiner* — Jessica Worsham
(74) *Attorney, Agent, or Firm* — Oblon, McClelland, Maier & Neustadt, L.L.P.

(57) ABSTRACT

Composition containing, in a cosmetically or dermatologically acceptable medium, a compound that may be obtained by reaction between:
an oil bearing at least one nucleophilic and/or electrophilic reactive function, and
a junction group capable of establishing hydrogen bonds with one or more partner junction groups, the junction group bearing at least one reactive function capable of reacting with the reactive function borne by the oil, and also comprising at least one unit of formula (I) or (II):

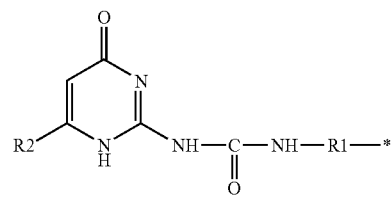

(I)

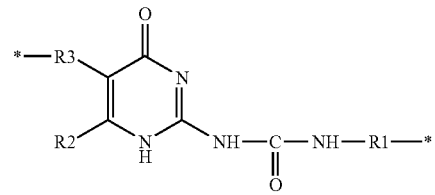

(II)

30 Claims, No Drawings

COMPOSITION CONTAINING A COMPOUND CAPABLE OF ESTABLISHING HYDROGEN BONDS, AND COSMETIC TREATMENT PROCESS

REFERENCE TO PRIOR APPLICATIONS

This application claims priority to U.S. provisional application Ser. No. 61/080,283, filed Jul. 14, 2008; and to French patent application 08 54556, filed Jul. 4, 2008, both incorporated herein by reference.

FIELD OF THE INVENTION

The present invention relates generally to a composition, preferably a cosmetic or dermatological composition, especially a composition for caring for, treating and/or making up keratin materials, comprising novel compounds capable of establishing hydrogen bonds with partner junction groups, the compounds making it possible to obtain a "long-lasting" effect for a deposit formed on the keratin materials, the "long-lasting" effect possibly being associated with the colour fastness, the gloss fastness, the staying power per se, possibly associated with a "non-tacky" and/or "transfer-resistance" effect.

DISCUSSION OF THE BACKGROUND

Many cosmetic compositions exist for which gloss properties of the deposited film, after application to keratin materials, are desired. Mention may be made, for example, of lipsticks or nail varnishes. In order to obtain such a result, it is possible to combine particular starting materials, especially lanolins, with "glossy" oils such as polybutenes, or esters of fatty acid or of fatty alcohol with a high carbon number; or alternatively certain plant oils; or alternatively esters resulting from the partial or total esterification of a hydroxylated aliphatic compound with an aromatic acid, as described in patent application EP 1 097 699.

To improve the gloss and the staying power over time of the deposited film, it has also been proposed to use oils of triglyceride type, in the present case castor oil, functionalized with isophorone diisocyanate (IPDI), as described in U.S. Pat. No. 5,707,612. Functionalization with IPDI substantially improves the staying power and the gloss of castor oil; the oils thus crosslinked find an application especially in the field of lipsticks.

However, it has been found that although these crosslinked oils give the deposit staying power and gloss, they do not make it possible to obtain on the keratin substrate a homogeneous, cohesive deposit that forms a uniform film and that is also non-tacky and transfer-resistant.

One aim of the present invention is to propose cosmetic compositions for obtaining such a uniform film-forming deposit on the substrate, the film combining gloss, gloss fastness and staying power of the composition, while at the same time being non-tacky and particularly comfortable to wear.

DETAILED DESCRIPTION OF THE PREFERRED EMBODIMENTS

One subject of the present invention is thus a composition comprising, in a cosmetically or dermatologically acceptable medium, a compound that may be obtained, or is obtained, by reaction between:

an oil bearing at least one nucleophilic and/or electrophilic reactive function, and
a junction group capable of establishing hydrogen bonds with one or more partner junction groups, each junction group pairing involving at least 3 hydrogen bonds, the junction group bearing at least one reactive function capable of reacting with the reactive function borne by the oil, the junction group also comprising at least one unit of formula (I) or (II) as defined hereinbelow.

As used herein, the phrase "a compound that may be obtained by reaction . . . " is not limited by the noted reaction and refers to a chemical product capable of being obtained by the noted reaction but not necessarily being so obtained. As is generally known in the art, there typically exists more than one synthetic pathway to a given compound, such pathways being readily envisioned by those of ordinary skill in the art given the noted reaction and/or structure of the compound and/or its reactants.

As used herein, the phrase "a compound that is obtained by reaction . . . " is limited by the noted reaction and refers to a chemical product obtained by the noted reaction.

The functionalized oils according to the present invention are in the form of a solid; this makes it possible especially to form a non-tacky material, which does not transfer onto the fingers when applied to a keratin substrate; this is not the case for the functionalized oils of the prior art, especially as described in U.S. Pat. No. 5,707,612, which are in the form of a more or less viscous liquid, and which form a tacky material that transfers onto the fingers after application to a substrate.

Moreover, it has been found that crosslinking via 4 hydrogen bonds, by means of ureidopyrimidone groups, can increase the force of this crosslinking, and thus improve the staying power of the desired cosmetic effect, most particularly the staying power of the deposit or the gloss fastness.

Moreover, the compounds or functionalized oils according to the invention can be readily conveyed in the usual cosmetic media, especially the usual oily cosmetic media.

They are advantageously compatible with the oils usually present in cosmetic compositions, and also have good dispersing properties towards pigments or fillers.

They can be readily conveyed in cosmetic solvent-based or oily media, especially oils, fatty alcohols and/or fatty esters, which facilitates their use in the cosmetic field, especially in lipsticks. They have suitable solubility in varied cosmetic oily media, such as plant oils, alkanes, esters, whether they are short such as butyl or ethyl acetate, or fatty, fatty alcohols and most particularly in media comprising isododecane, Parleam, isononyl isononanoate, octyldodecanol and/or a $C_{12}$-$C_{15}$ alkyl benzoate.

The cosmetic compositions according to the invention moreover have good applicability and good covering power; good adhesion to the support, whether it is to the nails, the eyelashes, the skin or the lips; adequate flexibility and strength of the film, and also an excellent level of long-lasting gloss. The comfort and glidance properties are also very satisfactory.

The compounds according to the invention may be obtained by reaction between:

on the one hand, at least one oil bearing at least one nucleophilic and/or electrophilic reactive function, and
on the other hand, at least one junction group capable of establishing hydrogen bonds with one or more partner junction groups, each junction group pairing involving at least 3 hydrogen bonds, the junction group bearing at least one reactive function capable of reacting with the reactive function borne by the oil, the junction group comprising at least one unit of formula (I) or (II) as defined hereinbelow.

Preferably, the compounds according to the invention may be obtained by reaction between:
- on the one hand, at least one oil bearing at least one nucleophilic reactive function chosen from OH and $NH_2$, and
- on the other hand, at least one junction group capable of establishing hydrogen bonds with one or more partner junction groups, each junction group pairing involving at least 3 hydrogen bonds, the junction group bearing at least one isocyanate or imidazole reactive function, the junction group comprising at least one unit of formula (I) or (II) as defined hereinbelow.

In conclusion, the compounds according to the invention thus comprise at least one part (HB) originating from the oil and at least one part (G) originating from the junction group, the part (G) comprising at least one unit of formula (I) or (II).

In particular, the parts (HB) and (G) are connected via a covalent bond and may especially be connected via a covalent bond formed during the reaction between the OH and/or $NH_2$ reactive functions borne by the oil and the isocyanate reactive functions borne by the junction group; or alternatively between the $NH_2$ reactive functions borne by the oil and the isocyanate or imidazole functions borne by the junction group.

The preferential production of the compounds according to the invention may thus especially be represented schematically by the chemical reaction between the following species:

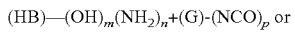

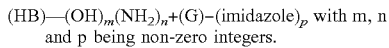

and p being non-zero integers.

The oil that may be used to prepare the compound according to the invention, which may preferably be represented schematically as $(HB)-(OH)_m(NH_2)_n$, is a fatty substance or a mixture of fatty substances, which is not crystalline at 25° C., and is liquid at room temperature and at atmospheric pressure (25° C., 1 atm.); preferably apolar or even, preferably, water-insoluble.

The term "liquid" means that the viscosity of the compound is less than or equal to 2500 centipoises, at 110° C. and 1 atm., measured with a Brookfield DV-I or Brookfield Cap 1000+ rheometer, a person skilled in the art selecting the machine that is suited to the viscosity measurement.

The term "apolar" means a compound whose HLB value (hydrophilic/lipophilic balance) is low; especially less than or equal to 8, preferably less than or equal to 4 and better still less than or equal to 2; preferentially, the HLB value should be low enough to make it possible to obtain a supramolecular material that is not hygroscopic, or not too hygroscopic.

The term "insoluble" means that the oil fraction that can dissolve in water, at 25° C. and 1 atm., is less than 5% by weight (i.e. 5 g of oil in 100 ml of water); preferably less than 3%.

The term "fatty substance" means especially, but not exclusively, a hydrocarbon-based compound comprising one or more saturated or unsaturated, linear, cyclic or branched alkyl chains, containing at least 6 carbon atoms and possibly comprising polar groups such as an acid, hydroxyl or polyol, amine, amide, phosphoric acid, phosphate, ester, ether, urea, carbamate, thiol, thioether or thioester group, this chain possibly containing up to 100 carbon atoms.

Preferably, the oil that may be used to prepare the compound according to the invention is a glossy oil, i.e. an oil with a refractive index of greater than or equal to 1.46 at 25° C. and in particular between 1.46 and 1.55 (the refractive index being defined relative to the sodium D line, at 25° C.).

Preferably, the oil that may be used to prepare the compound according to the invention is a non-volatile oil. The term "non-volatile oil" means an oil that is capable of remaining on keratin materials at room temperature and atmospheric pressure for at least several hours, and that especially has a vapour pressure of less than $10^{-3}$ mmHg (0.13 Pa).

Preferably, the oil has a molar mass (Mw) of between 150 and 6000, especially between 170 and 4000, or even between 180 and 2000, more preferentially between 200 and 1500 and better still between 220 and 800 g/mol.

The oil that may be used in the context of the present invention bears at least one reactive function capable of reacting with the reactive function borne on the junction group, and is especially capable of reacting chemically with the isocyanate or imidazole groups borne by the junction group; preferably, this function is an OH or $NH_2$ function. Preferably, the oil comprises only OH functions, in particular 1 to 3 OH functions, preferentially primary or secondary OH functions, and better still only primary functions.

The oil according to the present invention is preferably a carbon-based and especially a hydrocarbon-based oil, which, besides the reactive function capable of reacting with the junction group, may comprise oxygen, nitrogen, sulfur and/or phosphorus atoms. The oil is very preferentially chosen from cosmetically acceptable oils.

The oil that may be used in the context of the present invention may be chosen from:
(i) saturated or unsaturated, linear, branched or cyclic fatty alcohols containing 6 to 50 carbon atoms, comprising one or more OH; optionally comprising one or more $NH_2$.

Mention may be made in particular of:
- saturated or unsaturated, linear or branched $C_6$-$C_{50}$, especially $C_6$-$C_{32}$ and in particular $C_8$-$C_{28}$ monoalcohols, and especially isostearyl alcohol, cetyl alcohol, oleyl alcohol, isopalmitoyl alcohol, 2-butyloctanol, 2-hexyldecanol, 2-octyldecanol, 2-octyldodecanol, 2-octyltetradecanol, 2-decyltetradecanol and 2-dodecylhexadecanol, and especially the alcohols sold under the name Jarcol by the company Jarchem Industries, such as Jarcol 1-12, Jarcol 1-16, Jarcol 1-20 and Jarcol 1-24;
- saturated or unsaturated, linear or branched $C_6$-$C_{50}$, especially $C_6$-$C_{40}$ and in particular $C_8$-$C_{38}$ diols, and especially branched $C_{32}$-$C_{36}$ diols, and in particular the commercial product Pripol 2033 from Uniqema;
- saturated or unsaturated, linear or branched $C_6$-$C_{50}$, especially $C_6$-$C_{32}$ and in particular $C_8$-$C_{28}$ triols, and especially phytanetriol;

(ii) esters and ethers bearing at least one free OH, and especially partial polyol esters and ethers, and hydroxylated carboxylic acid esters.

The term "partial polyol ester" means esters prepared by esterification of a polyol with a substituted or unsubstituted carboxylic acid, the reaction not being total, i.e. not performed on all of the free OHs of the polyol; as a result, the ester thus still comprises at least one free OH.

Preferably, the carboxylic acid is a monoacid. A mixture of carboxylic acids, especially monocarboxylic acids, may also be used.

The term "partial polyol ether" means ethers prepared by etherification of a polyol, with itself or with at least one other monohydroxylated or polyhydroxylated alcohol, preferably a monoalcohol, the etherification reaction not being total, i.e. not performed on all of the free OHs of the polyol; as a result, the ether still comprises at least one free OH.

The term "hydroxylated carboxylic acid ester" means (mono and poly)esters prepared by reaction between a carboxylic acid bearing at least one free OH function, and one or more (mono or poly)alcohols, preferably a monoalcohol, the reaction possibly being total or partial (performed on all or some of the free OHs of the alcohol).

Among the polyols that may be used for preparing the above esters or ethers, mention may be made of propylene glycol, glycerol, neopentyl glycol, trimethylolpropane, trimethylolethane, polyglycerols and especially polyglycerol-2, polyglycerol-3 and polyglycerol-10; erythritol, dipentaerythritol, pentaerythritol, bis(trimethylolpropane), phytanetriol, sucrose, glucose, methylglucose, sorbitol, fructose, xylose, mannitol or glucosamine; and also diol dimers obtained especially from fatty acid dimers, especially branched aliphatic and/or alicyclic $C_{32}$-$C_{38}$ and especially $C_{36}$ diols, such as those defined in the article Hofer et al., European Coating Journal (March 2000), pages 26-37; and mixtures thereof.

Among the monoalcohols that may be used for preparing the above esters or ethers, mention may be made of linear or branched, preferably branched, $C_3$-$C_{50}$ alcohols, and especially 2-ethylhexanol, octanol and isostearyl alcohol, and mixtures thereof.

Among the carboxylic acids that may be used for preparing the above esters or ethers, mention may be made of linear or branched, saturated or unsaturated monoacids containing 6 to 50 carbon atoms and diacids containing 3 to 12 carbon atoms, among which mention may be made of octylneodecanoic acid, hexyldecanoic acid, ethylhexanoic acid, isostearic acid, nonanoic acid, isononanoic acid, arachidic acid, stearic acid, palmitic acid, oleic acid, oxalic acid, adipic acid, succinic acid, fumaric acid, maleic acid, capric acid, hexanedioic acid and decanoic acid, and mixtures thereof.

Among the hydroxylated carboxylic acids that may be used for preparing the above esters or ethers, mention may be made of monohydroxylated or polyhydroxylated acids, preferably monohydroxylated acids, containing for example 4 to 28 carbon atoms, and especially 12-hydroxystearic acid, ricinoleic acid, malic acid, lactic acid and citric acid; and mixtures thereof.

Thus, the oil that may be used in the present invention may be chosen, alone or as a mixture, from:
  pentaerythritol partial esters, and especially pentaerythrityl adipate, pentaerythrityl caprate, pentaerythrityl succinate, pentaerythrityl tetraisononanoate, pentaerythrityl triisononanoate, pentaerythrityl tetraisostearate, pentaerythrityl triisostearate, pentaerythrityl 2-(tetradecyl)-tetradecanoate, pentaerythrityl (tetraethyl)hexanoate and pentaerythrityl (tetraoctyl)dodecanoate;
  dipentaerythritol diesters, triesters, tetraesters or pentaesters, and especially dipentaerythrityl pentaisononanoate, dipentaerythrityl pentaisostearate, dipentaerythrityl tetraisostearate and dipentaerythrityl tris(polyhydroxystearate);
  trimethylolpropane monoesters and diesters, for instance trimethylolpropane monoisostearate, trimethylolpropane diisostearate, trimethylolpropane mono-2-ethylhexanoate and trimethylolpropane bis(2-ethylhexanoate);
  bis(trimethylolpropane) monoesters, diesters and triesters, for instance bis(trimethylolpropane) diisostearate, bis(trimethylolpropane) triisostearate and bis(trimethylolpropane) triethylhexanoate;
  partial monoesters or polyesters of glycerol or of polyglycerols, and especially:
    glyceryl diisostearate and glyceryl diisononanoate;
    polyglycerol-2 monoesters, diesters and triesters; for example with isostearic acid, 2-ethylhexanoic acid and/or isononanoic acid; and especially polyglyceryl-2 isostearate; polyglyceryl-2 diisostearate; polyglyceryl-2 triisostearate;
  polyglyceryl-2 nonaisostearate; polyglyceryl-2 nonanoate; polyglycerol-3 monoesters, diesters, triesters or tetraesters; for example with either isostearic acid, 2-ethylhexanoic acid and/or isononanoic acid; and especially polyglyceryl-3 isostearate; polyglyceryl-3 diisostearate; polyglyceryl-3 triisostearate;
  polyglyceryl-3 nonaisostearate; polyglyceryl-3 nonanoate;
  polyglycerol-10 partial esters and in particular polyglyceryl-10 nonaisostearate; polyglyceryl-10 nonanoate; polyglyceryl-10 isostearate; polyglyceryl-10 diisostearate; polyglyceryl-10 triisostearate;
  propylene glycol monoesters, for instance propylene glycol monoisostearate, propylene glycol neopentanoate or propylene glycol monooctanoate;
  diol dimer monoesters, for instance isostearyl dimer dilinoleate and octyldodecyl dimer dilinoleate;
  glycerol ethers, such as polyglyceryl-2 oleyl ether, polyglyceryl-3 cetyl ether, polyglyceryl-3 decyl tetradecyl ether and polyglyceryl-2 stearyl ether;
  esters between a hydroxylated monocarboxylic, dicarboxylic or tricarboxylic acid and monoalcohols, and in particular:
    esters, especially monoesters, of 12-hydroxystearic acid; such as octyl hydroxystearate and 2-octyldodecyl hydroxystearate; mention may also be made of the corresponding oligomeric polyhydroxy-stearates, especially having a degree of polymerization of from 1 to 10, bearing at least one residual OH;
  lactic acid esters, and especially C4-40 alkyl lactates, such as 2-ethylhexyl lactate, diisostearyl lactate, isostearyl lactate, isononyl lactate or 2-octyldodecyl lactate;
  malic acid esters, and especially C4-40 alkyl malates, such as bis(2-ethylhexyl) malate, diisostearyl malate or bis(2-octyldodecyl) malate;
  citric acid esters, and especially C4-40 alkyl citrates, such as triisostearyl citrate, triisocetyl citrate and triisoarachidyl citrate;
(iii) hydroxylated natural oils, modified natural oils and plant oils, and especially:
  triglyceryl esters bearing one or more OHs;
  hydrogenated or non-hydrogenated castor oil, and also derivatives thereof derived especially from the transesterification of castor oil; for instance the products Polycin M-365 or Polycin 2525 sold by Vertellus;
  modified epoxidized oils, the modification consisting in opening the epoxy function to obtain a diol, and especially hydroxylated modified soybean oil; hydroxylated soybean oils (directly hydroxylated or epoxidized beforehand); and especially the oils Agrol 2.0, Agrol 3.0 and Agrol 7.0 sold by Bio-Based Technologies, LLC; the oil Soyol R2-052 from the company Urethane Soy System; the Renuva oils sold by Dow Chemical; the oils BioH Polyol 210 and 500 sold by Cargill.

In particular, when glossy oils are used, the following glossy oils, the refractive index of which at 25° C. is indicated in parentheses, may be used: polyglyceryl-3 diisostearate (1.472), phytanetriol (1.467), castor oil (1.475), 2-octyldodecanol (1.46), oleyl alcohol (1.461), octyl hydroxystearate (1.46), polyglyceryl-2 isostearate (1.468), polyglyceryl-2 diisostearate (1.464), diisostearyl malate (1.462), 2-butyloctanol, 2-hexyldecanol (1.45), 2-decyltetradecanol (1.457), and also mixtures thereof.

Preferably, the oils that may be used in the present invention are chosen from 2-octyldodecanol, diisostearyl malate, 2-butyloctanol, 2-hexyldecanol, 2-decyltetradecanol; hydrogenated or non-hydrogenated castor oil, and also derivatives thereof; hydroxylated modified soybean oil, and mixtures thereof.

The junction group that may be used to form the compound according to the invention bears at least one reactive group, especially isocyanate or imidazole, capable of reacting with the reactive functions, especially OH and/or $NH_2$ (exclusively $NH_2$ for imidazole), of the oil, in order to form a covalent bond, especially of urethane type, between the oil and the junction group.

The junction group is capable of establishing H bonds with one or more partner junction groups, of identical or different chemical nature, each junction group pairing involving at least 3H (hydrogen) bonds, preferably at least 4H bonds and preferentially 4H bonds.

For the purposes of the invention, the term "junction group" means any functional group comprising groups that are H bond donors or acceptors, and that are capable of establishing at least 3H bonds, preferably at least 4H bonds, preferentially 4H bonds, with an identical or different partner junction group.

For the purposes of the invention, the term "partner junction group" means any junction group that can establish H bonds with one or more junction groups of the same or of another polymer according to the invention. The junction groups may be of identical or different chemical nature. If they are identical, they may then establish H bonds between themselves and are then referred to as self-complementary junction groups. If they are different, they are chosen such that they are complementary with respect to H interactions.

The junction group, bearing isocyanate groups, may thus be represented schematically as $(G)(NCO)_p$, p being a non-zero integer, preferably equal to 1 or 2.

The junction group moreover comprises at least one monovalent unit of formula (I) and/or at least one divalent unit of formula (II), as defined below:

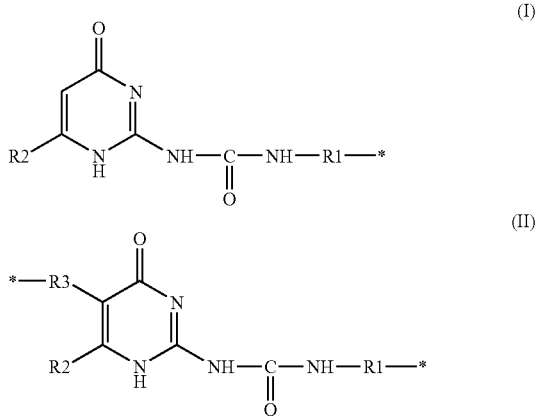

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a hydrogen atom or a linear, branched or cyclic, saturated or unsaturated, optionally aromatic, $C_1$-$C_{32}$ carbon-based and especially hydrocarbon-based (alkyl) radical, which may comprise one or more heteroatoms chosen from O, N, S, F, Si and P.

The radical R1 may especially be:
a linear or branched, divalent $C_2$-$C_{12}$ alkylene group, especially a 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene) or 1,7-(3,7-dimethyloctylene) group;
a divalent $C_4$-$C_{12}$ cycloalkylene or arylene group, chosen especially from the following radicals: -isophorone-, tolylene, 2-methyl-1,3-phenylene, 4-methyl-1,3-phenylene; 4,4'-methylenebiscyclohexylene; 4,4-bisphenylenemethylene; or of structure:

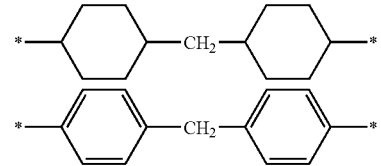

The term "-isophorone-" means the divalent radical having the structure:

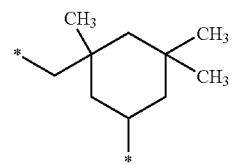 [SMILES: *CC1(C)CC(*)CC(C)(C)C1]

Preferentially, R1 represents -isophorone-, —$(CH_2)_6$— or 4,4'-methylenebiscyclohexylene.

The radical R2 may especially be H or:
a $C_1$-$C_{32}$, in particular $C_1$-$C_{16}$ or even $C_1$-$C_{10}$ alkyl group;
a $C_4$-$C_{12}$ cycloalkyl group;
a $C_4$-$C_{12}$ aryl group;
a ($C_4$-$C_{12}$)aryl($C_1$-$C_{18}$)alkyl group;
a $C_1$-$C_4$ alkoxy group;
an arylalkoxy group, in particular an aryl($C_1$-$C_4$)alkoxy group;
a $C_4$-$C_{12}$ heterocycle;
or a combination of these radicals, which may be optionally substituted with an amino, ester and/or hydroxyl function.

Preferably, R2 represents H, $CH_3$, ethyl, $C_{13}H_{27}$, $C_7H_{15}$, phenyl, isopropyl, isobutyl, n-butyl, tert-butyl, n-propyl or —$CH(C_2H_5)(C_4H_9)$.

Preferably, R3 represents a divalent radical —R'3-O—C(O)—NH—R'4- in which R'3 and R'4, which may be identical or different, represent a divalent carbon-based radical chosen from a linear or branched $C_1$-$C_{32}$ alkyl group, a $C_4$-$C_{16}$ cycloalkyl group and a $C_4$-$C_{16}$ aryl group; or a mixture thereof.

In particular, R'3 and R'4 may represent methylene, 1,2-ethylene, 1,6-hexylene, 1,4-butylene, 1,6-(2,4,4-trimethylhexylene), 1,4-(4-methylpentylene), 1,5-(5-methylhexylene); 1,6-(6-methylheptylene); 1,5-(2,2,5-trimethylhexylene), 1,7-(3,7-dimethyloctylene); 4,4'-methylenebiscyclohexylene; 2-methyl-1,3-phenylene; 4-methyl-1,3-phenylene; 4,4'-bisphenylenemethylene; 1,2-tolylene, 1,4-tolylene, 2,4-tolylene, 2,6-tolylene; 1,5-naphthylene; tetramethylxylylene; isophorone.

Most particularly, R'3 may represent a C1-C4 alkylene, especially 1,2-ethylene.

Preferably, R'4 may represent the divalent radical derived from isophorone.

Most particularly, R3 may have the structure:

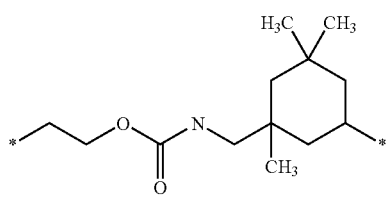 [SMILES: *CCOC(=O)NCC1(C)CC(*)CC(C)(C)C1]

In a particularly preferred manner, the following may apply in formula (I):

$R_1$=-isophorone-, R2=methyl, which gives the unit of formula:

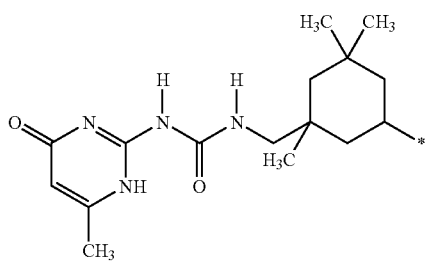

$R_1$=—$(CH_2)_6$—, R2=methyl, which gives the unit of formula:

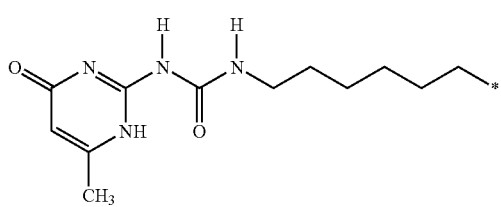

R1=—$(CH_2)_6$—, R2=isopropyl, which gives the unit of formula:

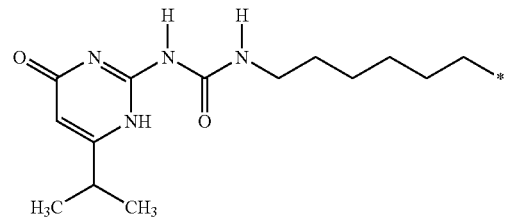

$R_1$=4,4'-methylenebiscyclohexylene and $R_2$ methyl, which gives the unit of formula:

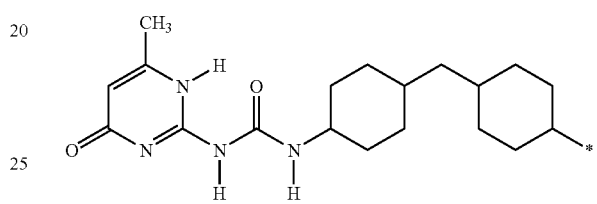

In a particularly preferred manner, in formula (II), R1 may represent the -isophorone-radical, R2=methyl and R3=—$(CH_2)_2OCO$—NH-isophorone-, which gives the divalent unit of formula:

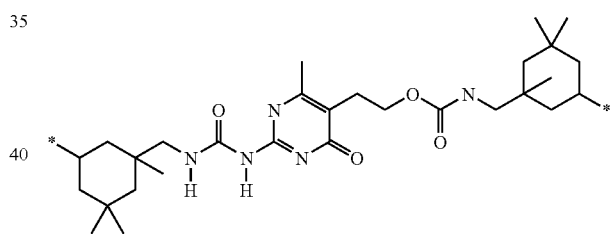

The junction groups bearing only one isocyanate function may have the formula:

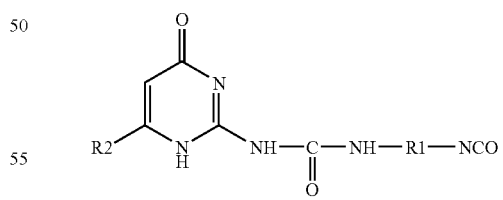

in which R1 and R2 are as defined above; and in particular:

R1 represents -isophorone-, —$(CH_2)_6$—, —$CH_2CH(CH_3)$—$CH_2$—$C(CH_3)_2$—$CH_2$—$CH_2$, 4,4'-methylenebiscyclohexylene or 2-methyl-1,3-phenylene; and/or R2 represents H, $CH_3$, ethyl, $C_{13}H_{27}$, $C_7H_{15}$, phenyl, isopropyl, isobutyl, n-butyl, tert-butyl, n-propyl or —CH$(C_2H_5)(C_4H_9)$.

Preferably, the junction groups may be chosen from the following groups:

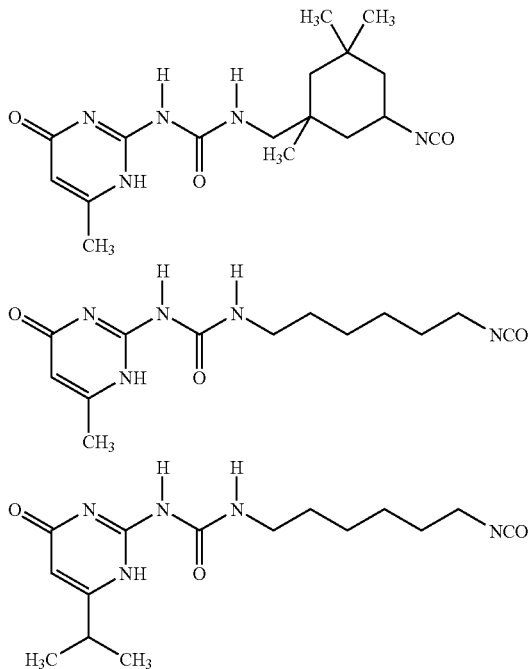

The junction groups bearing two isocyanate functions may have the formula:

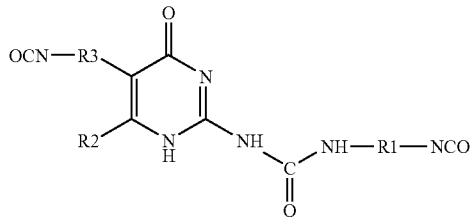

in which R1, R2 and R3 are as defined above, and in particular:

R1 represents -isophorone-, —(CH$_2$)$_2$—, —(CH$_2$)$_6$—, —CH$_2$CH(CH$_3$)—CH$_2$—C(CH$_3$)$_2$—CH$_2$—CH$_2$, 4,4'-methylenebiscyclohexylene or 2-methyl-1,3-phenylene; and/or R2 represents H, CH$_3$, ethyl, C$_{13}$H$_{27}$, C$_7$H$_{15}$, phenyl, isopropyl, isobutyl, n-butyl, tert-butyl, n-propyl or —CH(C$_2$H$_5$)(C$_4$H$_9$); and/or R3 represents a divalent radical —R'3-O—C(O)—NH—R'4- in which R'3 and R'4, which may be identical or different, represent a divalent carbon-based radical chosen from a linear or branched C$_1$-C$_{30}$ alkyl group, a C$_4$-C$_{12}$ cycloalkyl group and a C$_4$-C$_{12}$ aryl group; or a mixture thereof; and especially R'3 represents a C1-C4 alkylene, especially 1,2-ethylene, and R'4 represents the divalent radical derived from isophorone.

A junction groups that is most particularly preferred is the one having the formula:

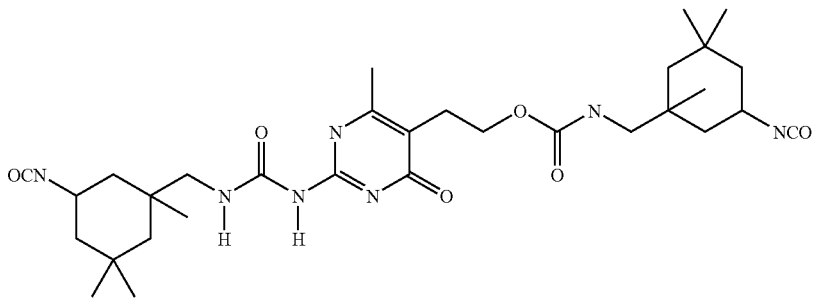

Among the junction groups bearing an imidazole group, mention may be made of the following compound:

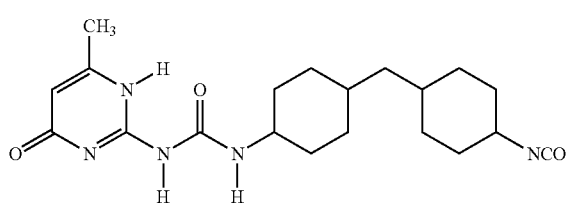

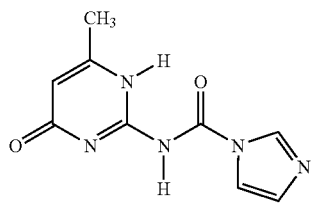 [SMILES: Cc1cc(=O)nc(NC(=O)n2ccnc2)[nH]1]

According to one particular embodiment of the invention, the junction groups may be attached to the oil by functionalization of the junction group with an isocyanate or imidazole.

According to another embodiment, it is possible to perform the reverse reaction by prefunctionalizing the oil with a diisocyanate.

As mentioned above (first mode), the compound according to the invention may thus result from the chemical reaction between an oil (HB)—(OH)$_m$(NH$_2$)$_n$ and a junction group (G)-(NCO)$_p$ or (G)-(imidazole)$_p$.

Preferably, the oil comprises only hydroxyl functions and the junction group comprises 1 or 2 isocyanate functions, which leads to the following reactions:

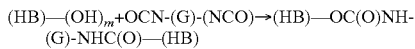

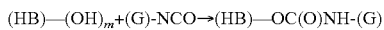

with m=integer greater than or equal to 1.

Preferably, the degree of grafting of the free OHs of the oil is between 1% and 100%, especially between 20% and 99% and better still between 50% and 95%; preferably, this degree is 100% (all the free OHs are functionalized with a junction group), especially when the oil initially comprises only one OH function.

The compound according to the invention may be prepared via the processes usually used by those skilled in the art for forming a urethane bond, between the free OH functions of the oil and the isocyanate functions borne by the junction group. By way of illustration, a general preparation process comprises:
  ensuring that the oil to be functionalized does not comprise any residual water,
  heating the oil comprising at least one reactive function, especially OH, to a temperature that may be between 60° C. and 140° C.;
  adding the junction group bearing the reactive functions, especially isocyanate;
  optionally stirring the mixture, under a controlled atmosphere, at a temperature of about 100-130° C.; for 1 to 24 hours;
  monitoring by infrared spectroscopy the disappearance of the characteristic band for isocyanates (between 2500 and 2800 cm$^{-1}$) so as to stop the reaction at the total disappearance of the peak, and then to allow the final product to cool to room temperature.

The reaction may be performed in the presence of a solvent, especially methyltetrahydrofuran, tetrahydrofuran, toluene or butyl acetate; the reaction may also be performed without solvent, in which case the oil may serve as solvent.

It is also possible to add a conventional catalyst for the formation of a urethane bond. An example that may be mentioned is dibutyltin dilaurate.

Finally, the compound may be washed and dried, or even purified, according to the general knowledge of a person skilled in the art.

According to the second embodiment, the reaction may include the following steps:

(i) functionalization of the oil with a diisocyanate according to the reaction scheme:

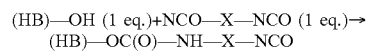

and then (iia) either reaction with 6-methylisocytosine:

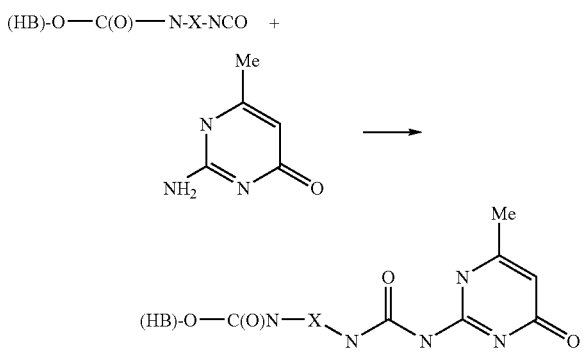

or (iib) or reaction with 5-hydroxyethyl-6-methylisocytosine:

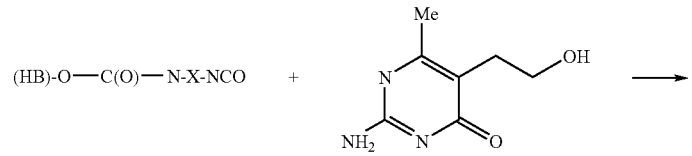

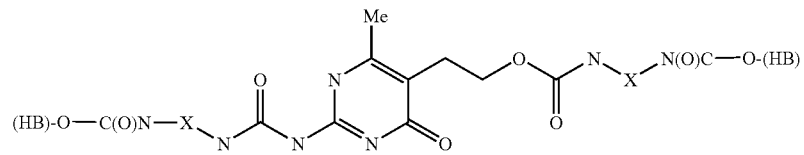

An illustration of such a reaction is given in Folmer et al., Adv. Mater., 12, 874-78 (2000).

The compounds according to the invention may especially correspond to the following structures:

ureidopyrimidone-functionalized octyldodecanol of structure:

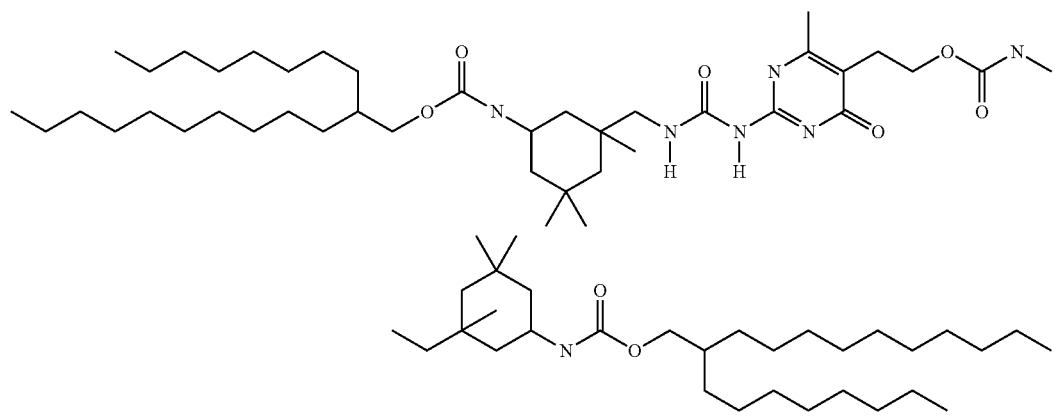
or of structure:
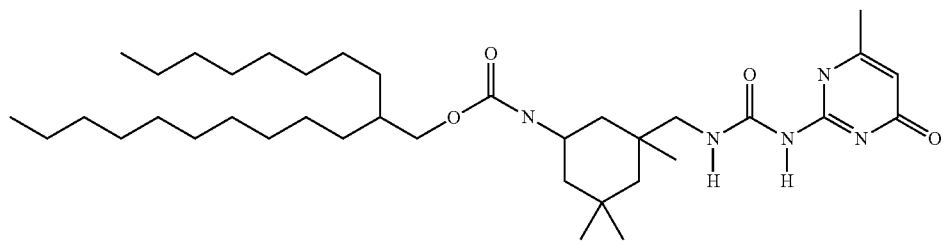 [SMILES: CCCCCCCCCCC(CCCCCCCC)COC(=O)NC1CC(C)(C)CC(C)(CNC(=O)Nc2nc(=O)cc(C)[nH]2)C1]
ureidopyrimidone-functionalized diisostearyl malate of structure:
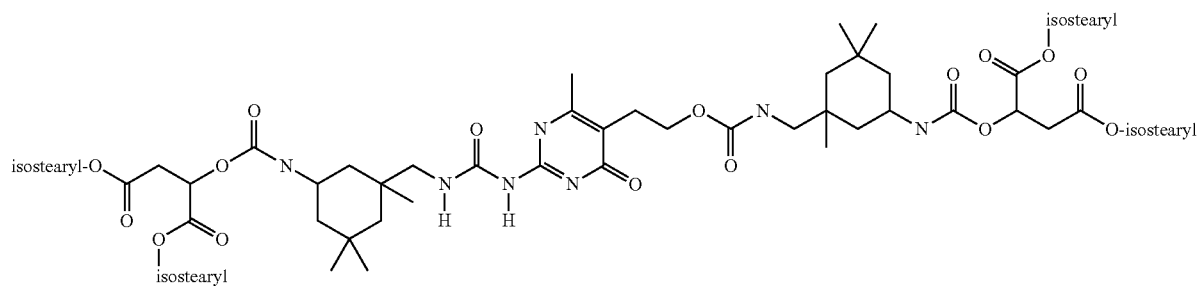
or of structure:
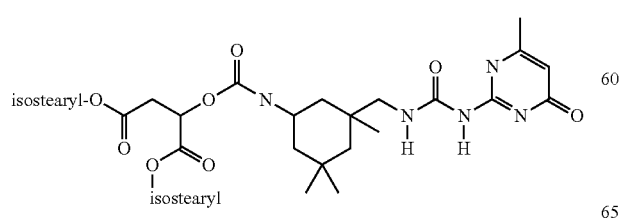

ureidopyrimidone-functionalized castor oil of structure:
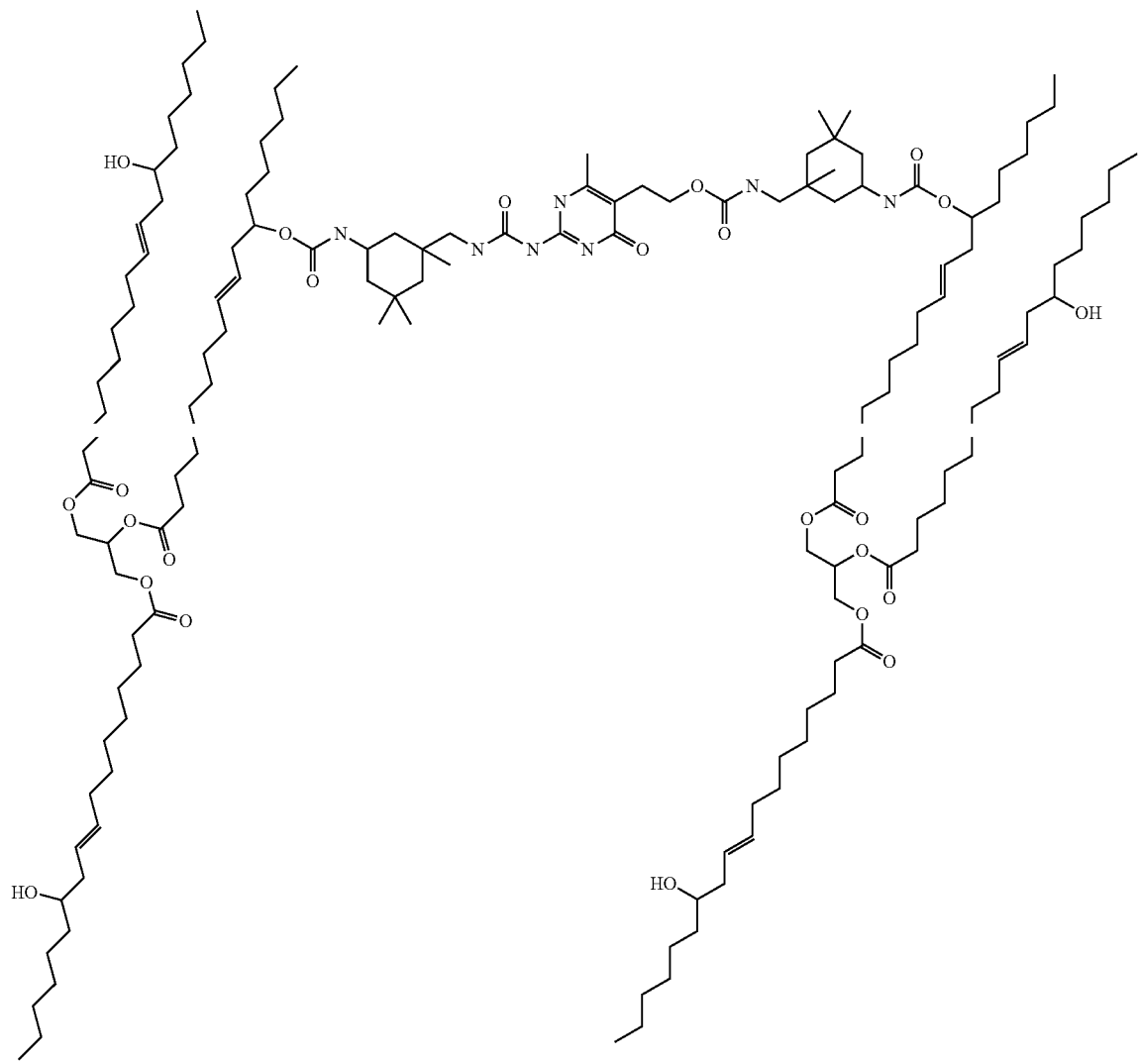

or of structure:
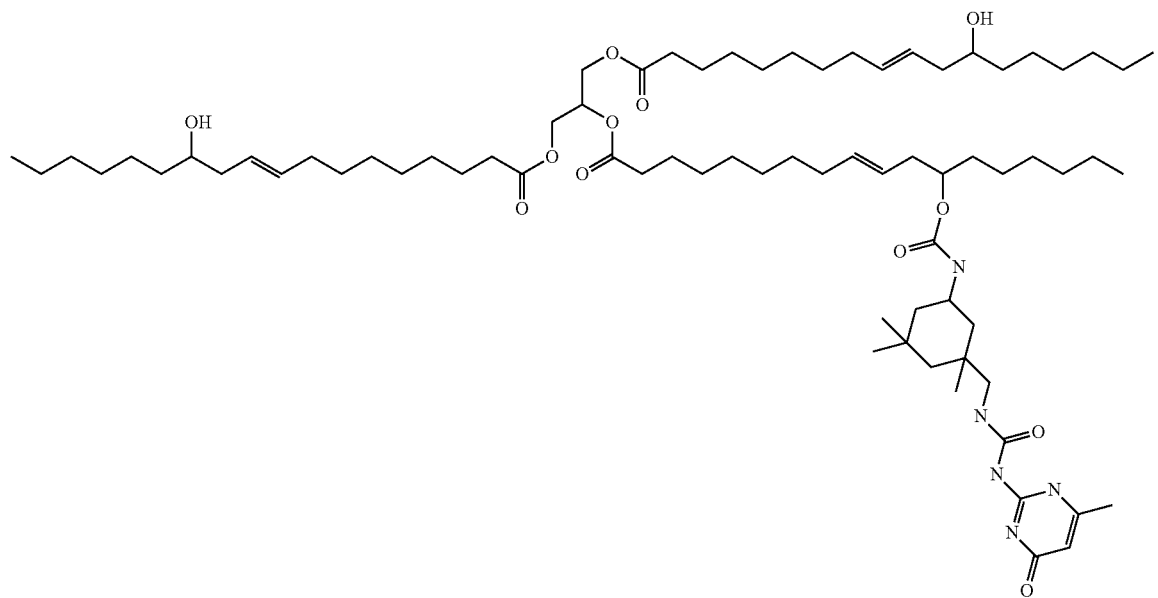 [SMILES: CCCCCCC(O)C/C=C/CCCCCCCC(=O)OCC(COC(=O)CCCCCCC/C=C/CC(O)CCCCCC)OC(=O)CCCCCCC/C=C/CC(CCCCCC)OC(=O)NC1CC(C)(C)CC(C)(CNC(=O)Nc2nc(=O)cc(C)[nH]2)C1]
ureidopyrimidone-functionalized 2-hexyldodecanol of structure:
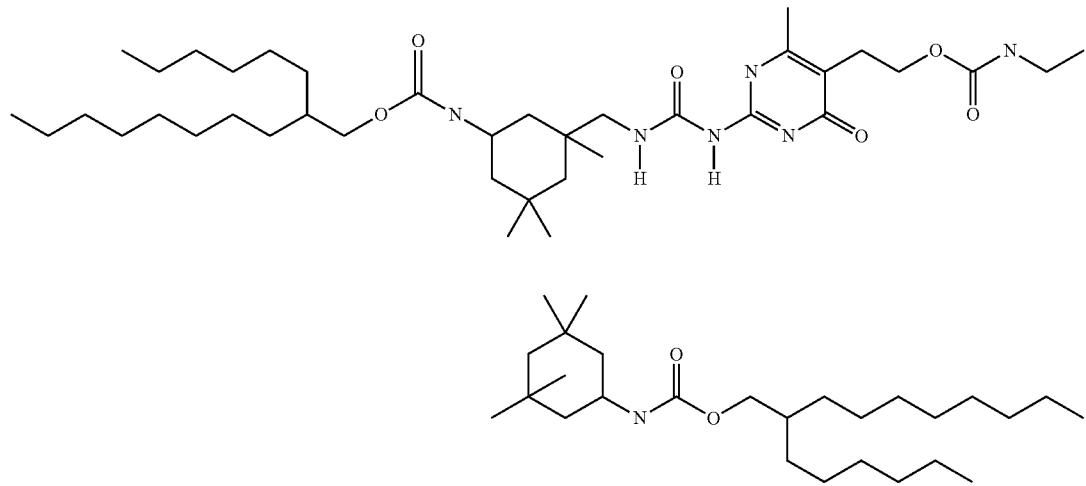
or of structure:
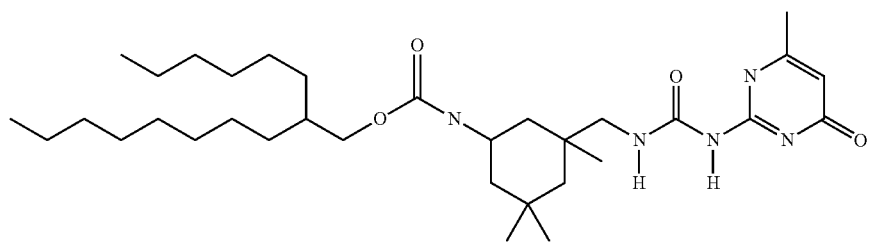 [SMILES: CCCCCCCCC(CCCCCC)COC(=O)NC1CC(C)(C)CC(C)(CNC(=O)Nc2nc(=O)cc(C)[nH]2)C1]

ureidopyrimidone-functionalized 2-decyltetradecanol of structure:

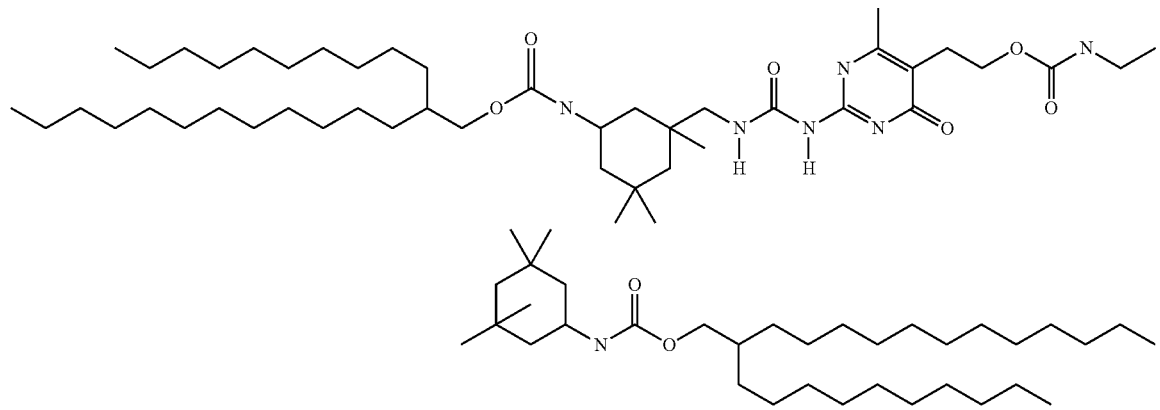

or of structure:

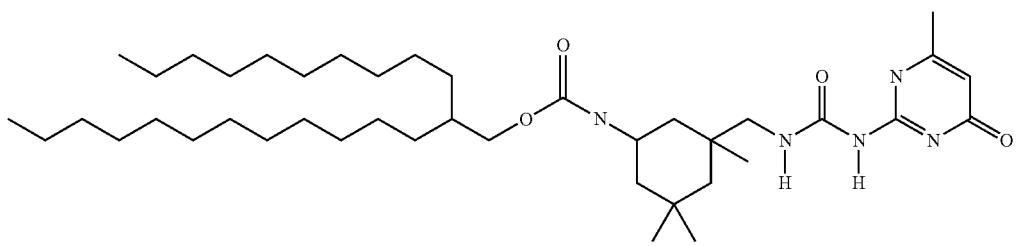 [SMILES: CCCCCCCCCCCCC(CCCCCCCCCC)COC(=O)NC1CC(C)(C)CC(C)(CNC(=O)Nc2nc(=O)cc(C)[nH]2)C1]

It has been found that the use of the compounds according to the invention may lead, after application of the composition to keratin materials, to the formation of a supramolecular polymer in the form of a physically crosslinked network, especially by means of hydrogen bonds, which is generally in the form of a film, and which has very good mechanical strength.

For the purposes of the invention, the term "supramolecular polymer" means a polymer chain or network formed from the assembly of non-polymers according to the invention with at least one other identical or different non-polymeric compound according to the invention, each assembly comprising at least one pair of identical or different paired junction groups.

For the purposes of the invention the term "pair of paired junction groups" means two junction groups, each of which may optionally be borne by the same compound according to the invention, the two groups being connected together via 4H bonds.

Thus, the supramolecular polymer will have points of physical crosslinking provided by the H bonds between these pairs of junction groups. The physical crosslinking will ensure the maintenance and persistence of the cosmetic effect in a similar manner to chemical crosslinking, while at the same time allowing reversibility, i.e. the possibility of totally removing the deposit.

Preferably, the compound according to the invention has a viscosity, measured at 125° C., of between 30 and 6000 mPa·s, especially between 150 and 4000 mPa·s, or even between 500 and 3500 mPa·s and better still between 750 and 3000 mPa·s.

The number-average molecular mass (Mn), measured in g/mol, of the compound according to the invention is preferably between 180 and 8000, preferably from 200 to 6000, or even from 300 to 4000, better still from 400 to 3000 and preferentially from 500 to 1500.

The compound according to the invention is advantageously soluble in the cosmetic oily media usually used, especially in plant oils, $C_6$-$C_{32}$ alkanes, $C_8$-$C_{32}$ fatty esters, $C_2$-$C_7$ short esters, $C_8$-$C_{32}$ fatty alcohols, and more particularly in media comprising at least isododecane, Parleam, isononyl isononanoate, octyldodecanol, a $C_{12}$-$C_{15}$ alkyl benzoate, butyl acetate or ethyl acetate, alone or as a mixture.

The term "soluble" means that the compound forms a clear solution in at least one solvent chosen from isododecane, Parleam, isononyl isononanoate, octyldodecanol, a $C_{12}$-$C_{15}$ alkyl benzoate, butyl acetate or ethyl acetate, in a proportion of at least 50% by weight, at 25° C.

The compounds according to the invention may be used advantageously in a cosmetic or dermatological composition, which moreover comprises a cosmetically or dermatologically acceptable medium, i.e. a medium that is compatible with keratin materials such as facial or bodily skin, the eyelashes, the eyebrows, the lips and the nails.

The amount of compound present in the compositions obviously depends on the type of composition and on the desired properties, and may vary within a very wide range, generally between 5% and 80% by weight, preferably between 10% and 75% by weight, especially between 20% and 70% by weight, or even between 25% and 65% by weight and better still between 30% and 60% by weight relative to the weight of the final cosmetic composition.

Depending on the envisaged application, the composition may then comprise the constituents that are common in this type of composition.

The composition according to the invention may advantageously comprise a liquid fatty phase, which may constitute a solvent medium for the polymers according to the invention, and which may comprise at least one compound chosen from volatile or non-volatile carbon-based, hydrocarbon-based, fluoro and/or silicone oils and/or solvents of mineral, animal, plant or synthetic origin, alone or as a mixture, provided that they form a stable homogeneous mixture and are compatible with the intended use.

For the purposes of the invention, the term "volatile" refers to any compound that is capable of evaporating on contact with keratin materials, or the lips, in less than one hour, at room temperature (25° C.) and atmospheric pressure (1 atm.). This volatile compound especially has a non-zero vapour pressure, at room temperature and atmospheric pressure, especially ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg). In contrast, the term "non-volatile" refers to a compound that remains on keratin materials or the lips at room temperature and atmospheric pressure, for at least one hour, and which especially has a vapour pressure of less than $10^{-3}$ mmHg (0.13 Pa).

Preferably, the physiologically acceptable medium of the composition according to the invention may comprise, in a liquid fatty phase, at least one oil and/or one solvent, which may be chosen, alone or as a mixture, from:

1) esters of monocarboxylic acids with monoalcohols and polyalcohols; advantageously, the ester is a $C_{12}$-$C_{15}$ alkyl benzoate or corresponds to the following formula: $R'_1$—COO—$R'_2$ in which:

$R'_1$ represents an optionally substituted, linear or branched alkyl radical of 1 to 40 carbon atoms and preferably from 7 to 19 carbon atoms, optionally comprising one or more ethylenic double bonds, the hydrocarbon-based chain of which may be interrupted with one or more heteroatoms chosen from N and O and/or one or more carbonyl functions, and $R'_2$ represents an optionally substituted, linear or branched alkyl radical of 1 to 40 carbon atoms, preferably from 3 to 30 carbon atoms and better still from 3 to 20 carbon atoms, optionally comprising one or more ethylenic double bonds, and the hydrocarbon-based chain of which may be interrupted with one or more heteroatoms chosen from N and O and/or one or more carbonyl functions.

The term "optionally substituted" means that $R'_1$ and/or $R'_2$ may bear one or more substituents chosen, for example, from groups comprising one or more heteroatoms chosen from O and/or N, such as amino, amine, alkoxy or hydroxyl.

Examples of groups $R'_1$ are those derived from fatty acids, preferably higher fatty acids, chosen from the group constituted by acetic acid, propionic acid, butyric acid, caproic acid, caprylic acid, pelargonic acid, capric acid, undecanoic acid, lauric acid, myristic acid, palmitic acid, stearic acid, isostearic acid, arachidic acid, behenic acid, oleic acid, linoleic acid, linolenic acid, oleostearic acid, arachidonic acid and erucic acid, and mixtures thereof.

Preferably, $R'_1$ is an unsubstituted branched alkyl group of 4 to 14 carbon atoms, preferably from 8 to 10 carbon atoms, and $R'_2$ is an unsubstituted branched alkyl group of 5 to 15 carbon atoms and preferably from 9 to 11 carbon atoms.

In particular, mention may preferably be made of $C_8$-$C_{48}$ esters, optionally incorporating in their hydrocarbon-based chain one or more heteroatoms chosen from N and C and/or one or more carbonyl functions; and more particularly purcellin oil (cetostearyl octanoate), isononyl isononanoate, isopropyl myristate, isopropyl palmitate, 2-ethylhexyl palmitate, 2-octyldodecyl stearate, 2-octyldodecyl erucate, isostearyl isostearate, $C_{12}$-$C_{15}$ alkyl benzoates, hexyl laurate or diisopropyl adipate; and heptanoates, octanoates, decanoates or ricinoleates of alcohols or of polyalcohols, for example of fatty alcohols, such as propylene glycol dioctanoate, and also isopropyl N-lauroyl sarcosinate (especially Eldew-205SL from Ajinomoto); hydroxylated esters, for instance isostearyl lactate or diisostearyl malate; and pentaerythritol esters; branched C8-C16 esters, especially isohexyl neopentanoate.

2) hydrocarbon-based plant oils with a high content of triglycerides, constituted of fatty acid esters of glycerol, the fatty acids of which may have varied chain lengths from C4 to C24, these chains possibly being linear or branched, and saturated or unsaturated; these oils are especially wheatgerm oil, corn oil, sunflower oil, shea oil, castor oil, sweet almond oil, macadamia oil, apricot oil, soybean oil, rapeseed oil, cottonseed oil, alfalfa oil, poppy seed oil, pumpkin oil, sesame seed oil, marrow oil, avocado oil, hazelnut oil, grapeseed oil, blackcurrant oil, evening primrose oil, millet oil, barley oil, quinoa oil, olive oil, rye oil, safflower oil, candlenut oil, passion flower oil, musk rose oil, jojoba oil, palm oil or beauty-leaf oil; or alternatively caprylic/capric acid triglycerides, such as those sold by the company Stearineries Dubois or those sold under the names Miglyol 810®, 812® and 818® by the company Dynamit Nobel.

3) C6-C32 and especially C12-C26 alcohols, and especially monoalcohols, for instance oleyl alcohol, linoleyl alcohol, linolenyl alcohol, isostearyl alcohol, 2-hexyldecanol, 2-butyloctanol, 2-undecylpentadecanol and octyldodecanol.

4) linear or branched, volatile or non-volatile hydrocarbon-based oils, of synthetic or mineral origin, which may be chosen from hydrocarbon-based oils containing from 5 to 100 carbon atoms, and especially petroleum jelly, polydecenes, hydrogenated polyisobutenes such as Parleam, squalane and perhydrosqualene, and mixtures thereof.

Mention may be made more particularly of linear, branched and/or cyclic C5-C48 alkanes, and preferentially branched $C_8$-$C_{16}$ alkanes, for instance $C_8$-$C_{16}$ isoalkanes of petroleum origin (also known as isoparaffins); especially decane, heptane, dodecane and cyclohexane; and also isododecane, isodecane and isohexadecane.

5) volatile or non-volatile silicone oils;

Volatile silicone oils that may be mentioned include volatile linear or cyclic silicone oils, especially those with a viscosity of less than 8 centistokes, and especially containing from 2 to 10 silicon atoms, these silicones optionally comprising alkyl or alkoxy groups containing from 1 to 22 carbon atoms; and in particular octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and methylhexyldimethylsiloxane, and mixtures thereof.

The non-volatile silicone oils that may be used according to the invention may be polydimethylsiloxanes (PDMS), polydimethylsiloxanes comprising alkyl or alkoxy groups, which are pendent and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Preferentially, the physiologically acceptable medium of the composition according to the invention comprises, in a liquid fatty phase, at least one oil and/or one solvent chosen, alone or as a mixture, from isododecane, Parleam, isononyl isononanoate, octyldodecanol, phenyl trimethicone, C12-C15 alkyl benzoates, butyl acetate, ethyl acetate and/or D5 (decamethylcyclopentasiloxane).

The liquid fatty phase may also comprise additional oils and/or solvents, which may be chosen, alone or as a mixture, from:
- fluoro oils such as perfluoropolyethers, perfluoroalkanes, for instance perfluorodecalin, perfluoroadamantanes, monoesters, diesters and triesters of perfluoroalkyl phosphates, and fluoro ester oils;
- oils of animal origin;
- $C_6$-$C_{40}$ and especially C10-C40 ethers; propylene glycol ethers that are liquid at room temperature, such as propylene glycol monomethyl ether, propylene glycol monomethyl ether acetate or dipropylene glycol mono-n-butyl ether;
- $C_8$-$C_{32}$ fatty acids, for instance oleic acid, linoleic acid or linolenic acid, and mixtures thereof;
- difunctional oils, comprising two functions chosen from ester and/or amide and containing from 6 to 30 carbon atoms, especially 8 to 28 carbon atoms and better still from 10 to 24 carbon atoms, and 4 heteroatoms chosen from O and N; the amide and ester functions preferably being in the chain;
- ketones that are liquid at room temperature (25° C.) such as methyl ethyl ketone, methyl isobutyl ketone, diisobutyl ketone, isophorone, cyclohexanone or acetone;
- aldehydes that are liquid at room temperature, such as benzaldehyde and acetaldehyde.

The liquid fatty phase may represent 1% to 90% by weight of the composition, especially from 5% to 75% by weight, in particular from 10% to 60% by weight or even from 25% to 55% by weight relative to the total weight of the composition.

The composition according to the invention may advantageously comprise a thickener, which may be chosen in particular from:
- silicas, especially hydrophobic silicas, such as those described in document EP-A-898 960, and sold, for example, under the references Aerosil R812® by the company Degussa, Cab-O-Sil TS-530®, Cab-O-Sil TS-610® and Cab-O-Sil TS-720® by the company Cabot, and Aerosil R972® and Aerosil R974® by the company Degussa;
- clays such as montmorillonite, and modified clays such as bentones, for example stearalkonium hectorite or stearalkonium bentonite;
- polysaccharide alkyl ethers (especially in which the alkyl group contains from 1 to 24, preferably from 1 to 10, better still from 1 to 6 and more especially from 1 to 3 carbon atoms) such as those described in document EP-A-898 958.

The amount of thickener in the composition according to the invention may range from 0.05% to 40% by weight, preferably from 0.5% to 20% and better still from 1% to 15% by weight relative to the total weight of the composition.

The composition according to the invention may also comprise at least one wax of plant, animal, mineral or synthetic origin, or even of silicone origin.

Mention may be made in particular, alone or as a mixture, of hydrocarbon-based waxes such as beeswax; carnauba wax, candelilla wax, ouricury wax, Japan wax, cork fibre wax or sugarcane wax; paraffin wax, lignite wax, microcrystalline waxes; lanolin wax; montan wax; ozokerites; polyethylene waxes; the waxes obtained by Fischer-Tropsch synthesis; hydrogenated oils, fatty esters and glycerides that are solid at 25° C. Silicone waxes may also be used, among which mention may be made of polymethylsiloxane alkyls, alkoxys and/or esters.

The amount of wax in the composition according to the invention may range from 0.1% to 70% by weight, preferably from 1% to 40% by weight and better still from 5% to 30% by weight relative to the total weight of the composition.

The composition according to the invention may also comprise one or more dyestuffs chosen from pulverulent compounds, for instance pigments, fillers, nacres and glitter flakes, and/or liposoluble or water-soluble dyes.

The dyestuffs, especially pulverulent dyestuffs, may be present in the composition in a content of from 0.01% to 50% by weight, preferably from 0.1% to 40% by weight or even from 1% to 30% by weight relative to the weight of the composition.

The term "pigments" should be understood as meaning white or coloured, mineral or organic particles of any shape, which are insoluble in the physiological medium, and which are intended to colour the composition.

The term "nacres" should be understood as meaning iridescent particles of any shape, produced especially by certain molluscs in their shell, or alternatively synthesized.

The pigments may be white or coloured, mineral and/or organic, and interference or non-interference pigments. Among the mineral pigments that may be mentioned are titanium dioxide, optionally surface-treated, zirconium oxide or cerium oxide, and also zinc oxide, iron oxide or chromium oxide, manganese violet, ultramarine blue, chromium hydrate and ferric blue. Among the organic pigments that may be mentioned are carbon black, pigments of D&C type and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment of the abovementioned type and also nacreous pigments based on bismuth oxychloride.

The fillers may be mineral or organic, and lamellar or spherical. Mention may be made of talc, mica, silica, kaolin, Nylon powders, poly-β-alanine powders and polyethylene powders, Teflon, lauroyllysine, starch, boron nitride, tetrafluoroethylene polymer powders, hollow microspheres such as Expancel (Nobel Industrie), Polytrap (Dow Corning) and silicone resin microbeads (for example Tospearls from Toshiba), precipitated calcium carbonate, magnesium carbonate, magnesium hydrogen carbonate, hydroxyapatite, hollow silica microspheres (Silica Beads from Maprecos), glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate.

The liposoluble dyes are, for example, Sudan red, DC Red 17, DC Green 6, β-carotene, soybean oil, Sudan brown, DC Yellow 11, DC Violet 2, DC Orange 5 or quinoline yellow. They may represent 0.01% to 20% and better still from 0.1% to 6% of the weight of the composition.

The water-soluble dyes are, for example, beetroot juice or methylene blue, and may represent 0.01% to 6% of the total weight of the composition.

The composition may also comprise other ingredients commonly used in cosmetic compositions. Such ingredients may be chosen from antioxidants, fragrances, essential oils, preserving agents, cosmetic active agents, moisturizers, vitamins, ceramides, sunscreens, surfactants, gelling agents, spreading agents, wetting agents, dispersants, antifoams, neutralizers, stabilizers, and polymers and especially liposoluble film-forming polymers, and mixtures thereof.

Needless to say, a person skilled in the art will take care to select this or these additional compound(s), and/or the amount thereof, such that the advantageous properties of the composition for the use according to the invention are not, or are not substantially, adversely affected by the envisaged addition.

The compositions according to the invention may be in any form that is acceptable and common for a cosmetic composition. They may thus be in the form of a suspension, a dispersion especially of oil in water by means of vehicles; an optionally thickened or even gelled organic or oily solution; an oil-in-water, water-in-oil or multiple emulsion; a gel or a mousse; an oily or emulsified gel; a dispersion of vesicles, especially lipid vesicles; a two-phase or multiphase lotion; a spray; a lotion, a cream, a pomade, a soft paste, an ointment, a cast or moulded solid, especially in stick or dish form, or a compacted solid.

A person skilled in the art may select the appropriate galenical form, and also the method for preparing it, on the basis of his general knowledge, taking into account firstly the nature of the constituents used, especially their solubility in the support, and secondly the intended use of the composition.

The compositions in accordance with the invention have improved gloss and improved fastness of the gloss when compared with the prior art, and may be used for caring for or making up keratin materials such as the skin, the eyelashes, the eyebrows, the nails or the lips, and more particularly for making up the lips, the eyelashes and/or the face.

They may thus be in the form of a product for caring for and/or making up bodily or facial skin, the lips, the eyelashes, the eyebrows or the nails; an antisun or self-tanning product; they are advantageously in the form of a makeup composition, especially a mascara, an eyeliner, a lipstick, a lip gloss, a makeup rouge, an eyeshadow, a foundation, a nail varnish or a nailcare product.

A subject of the invention is also a cosmetic process for treating keratin materials, especially bodily or facial skin, the lips, the nails and/or the eyelashes, comprising the application to the materials of a cosmetic composition as defined previously.

This process according to the invention especially allows the care or makeup of the keratin materials, in particular of the lips and/or the nails, by applying a composition, especially a lipstick, a lip gloss, a nailcare product or a nail varnish according to the invention.

The invention is illustrated in greater detail in the implementation examples that follow.

Example 1

Ureidopyrimidone-Functionalized Octyldodecanol

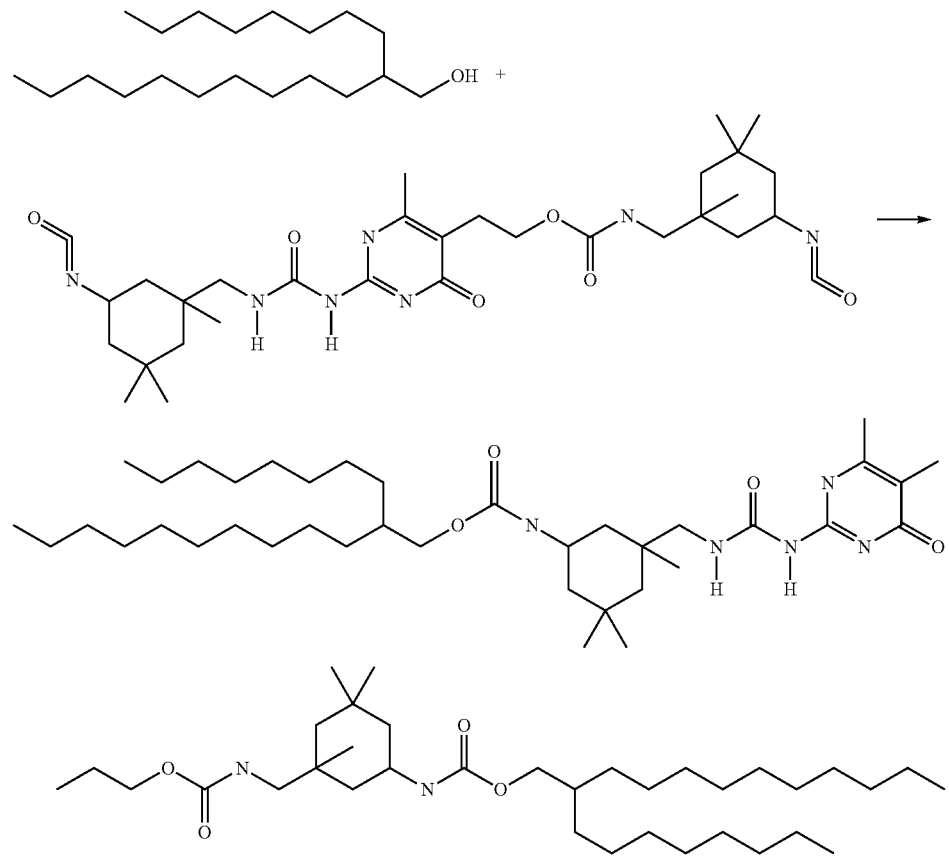

70 g of ureidopyrimidone diisocyanate are dissolved in methyltetrahydrofuran, under argon. 80.3 g of octyldodecanol in 100 ml of dichloromethane are added, under argon, followed by addition of 15 microliters of dibutyltin dilaurate (catalyst). The reaction mixture is refluxed until the isocyanate peak (2250-2265 cm$^{-1}$) has disappeared on IR spectrometry.

The excess octyldodecanol is removed by successive washing of the reaction medium with methanol, followed by three extractions and drying over MgSO$_4$. After evaporation of the organic phase, 103 g of a pale yellow powder, characterized by 1H NMR (structure in conformity), are obtained.

This powder may be conveyed in isododecane, for example at a concentration of 10% by weight; this concentration may especially be up to 60% by weight in isododecane, which then leads to a solution that is viscous but still manipulable. It is thus found that by functionalizing with a ureidopyrimidone, the oil changes from a liquid to a solid, which can be conveyed in isododecane at concentrations above 30%.

When a solution comprising 50% by weight of compound in isododecane is applied, after evaporating off the solvent, a glossy transparent film is obtained, which shows good adhesion by fragmentation, and low resistance to friction.

Example 2

Diisostearyl Malate Functionalized with a Ureidopyrimidone 15 g (0.0234 mol) of diisostearyl malate are dried under reduced pressure at 80° C. for 4 hours. 7.21 g (0.0117 mol) of ureidopyrimidone diisocyanate dissolved in 60 ml of methyltetrahydrofuran, and 12 µl of dibutyltin dilaurate catalyst are added. The mixture is heated at 95° C., under argon, for 26 hours (disappearance of the characteristic band for isocyanates on IR spectroscopy). 20 ml of methyltetrahydrofuran are added to the reaction mixture, and the resulting mixture is then filtered through Celite. After evaporating off the solvent and drying under reduced pressure, a pale yellow solid is obtained.

Example 3

Castor Oil Functionalized with a Ureidopyrimidone 15 g of castor oil (0.016 mol) are dried under reduced pressure at 80° C. for 4 hours. A solution of 4.9 g of ureidopyrimidone diisocyanate (0.008 mol) in 60 ml of methyltetrahydrofuran, and 12 µl of dibutyltin dilaurate catalyst are added. The mixture is heated at 90° C. for 19 hours (total disappearance of the characteristic band for isocyanates on IR spectroscopy). At the end of the reaction, the solvent is evaporated off and the resulting product is dried under reduced pressure at 35° C. overnight.

A pale yellow solid gum is obtained.

Example 4

Comparative to Example 1

Octyldodecanol Functionalized with Isophorone

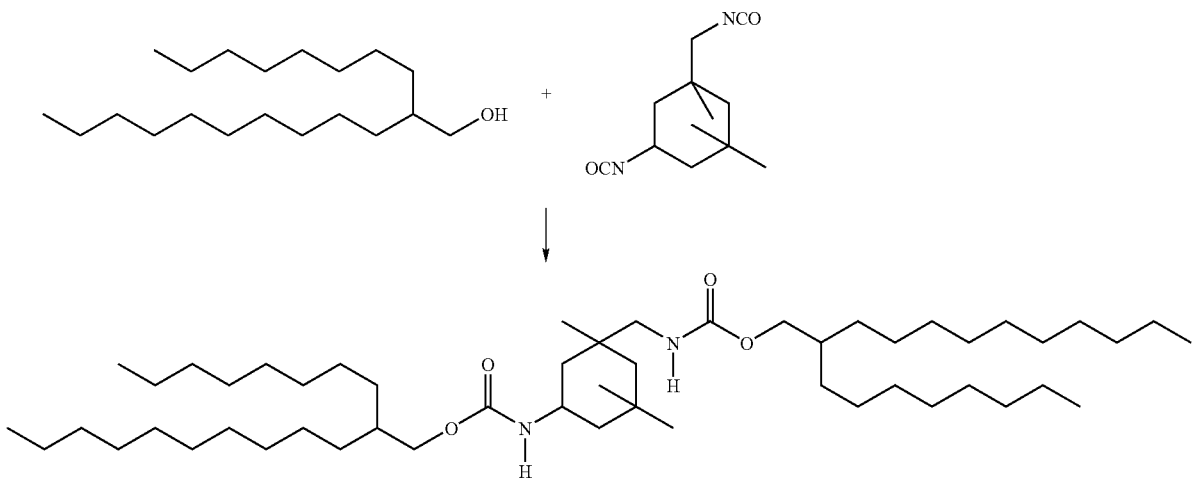

10 g of octyldodecanol are dried under reduced pressure at 80° C. for 2 hours, followed by addition of 3.72 g of isophorone diisocyanate and 25 microliters of dibutyltin dilaurate catalyst. The mixture is heated at 95° C. under argon. The disappearance of the isocyanate is monitored by IR spectroscopy (disappearance of the band between 2250 and 2265 cm$^{-1}$, after heating for 12 hours).

A viscous oil that does not form a cohesive material is obtained.

Example 5

Comparative to Example 2

Diisostearyl Malate Functionalized with Isophorone 10 g (0.0159 mol) of diisostearyl malate are dried under reduced pressure at 80° C. for 3 hours. 1.77 g (0.079 mol)

of isophorone diisocyanate and 2.5 µl of catalyst (dibutyltin dilaurate) are added under argon, and the reaction mixture is heated at 95° C. for 16 hours. During the reaction, the viscosity of the reaction medium increases. The reaction is stopped after disappearance of the characteristic peak for isocyanates on IR spectroscopy.

Example 6

Comparative to Example 3

Castor Oil Functionalized with Isophorone 15 g (0.016 mol) of castor oil are dried under reduced pressure at 80° C. for 6 hours. 1.78 g (0.008 mol) of isophorone diisocyanate and 12 µl of dibutyltin dilaurate catalyst are added, and the mixture is heated at 90° C. for 16 hours. The reaction is stopped after disappearance of the characteristic peak for isocyanates on IR spectroscopy.

Example 7

The compounds prepared in Examples 1 to 6 are observed, visually and by feel, and the results are summarized in the following table:

| | Physical appearance of the compound | Appearance of the film* Refractive index** (refractive index unfunctionalized oil) |
|---|---|---|
| Example 1 | Yellow solid | Glossy tacky film, which does not dewet; uniform deposit. No transfer onto the fingers. 1.488 (1.46) |
| Example 4 (comparative) | Transparent viscous oil | Film which dewets; non-uniform deposit. Transfers onto the fingers. 1.474 (1.46) |
| Example 2 | Yellow solid | Glossy, sparingly tacky film, which does not dewet; uniform deposit. No transfer onto the fingers. 1.478 (1.462) |
| Example 5 (comparative) | Transparent viscous oil | Glossy tacky film which dewets; non-uniform deposit. No transfer onto the fingers. 1.4598 (1.462) |
| Example 3 | Yellow solid (solid gum) | Glossy, slightly tacky film; behaviour of a fragile solid, which does not dewet; uniform deposit. No transfer onto the fingers. 1.4852 (1.48) |
| Example 6 (comparative) | Transparent viscous oil | Very tacky glossy film, which dewets; non-uniform deposit. Transfers onto the fingers. 1.4813 (1.48) |

*The films are formed from a solution containing 40% by weight of the compound, either in isododecane for Examples 1-2 and 4-5, or in tetrahydrofuran for Examples 3 and 6.
**For the refractive index measurements, all the films are formed from a solution containing 40% by weight of the compound in tetrahydrofuran; the refractive index is measured after evaporating off the solvent.

The term "film which does not dewet" means that, after deposition and evaporation of the solvent, a continuous, uniform "true" film is obtained.

The term "film which dewets" means that, after deposition and evaporation of the solvent, a non-uniform, discontinuous film "with holes" is obtained.

A tribometry test is performed on these deposits/films: the films are formed from a solution at 40% by weight in tetrahydrofuran, by deposition onto a nitrile elastomer, followed by drying for 24 hours at 25° C.

The tests are performed using a CSEM tribometer and equipped with a ball 6 mm in diameter. This ball, subjected to a 0.15 N load, rubs repeatedly on a film (10 to 20 µm thick). The rotation speed of the disk is set at 6.3 cm/s, which corresponds to a frequency of one revolution per second. The test is ended when wear is complete, or else is stopped after 1000 stress revolutions.

| | Observations |
|---|---|
| Example 1 | The film remains unchanged (uniform) for 300 revolutions (no wear or brittleness); the material is thus cohesive; behaviour of a solid. |
| Example 4 (comparative) | No measurement possible: the material has no cohesion, and behaves like an oil. |
| Example 2 | The film remains unchanged (uniform) for 1000 revolutions (no wear or brittleness); the material is thus cohesive and does not wear out |
| Example 5 (comparative) | The material behaves like an oil, with a buttering effect when it is subjected to the wear test. |
| Example 3 | The film is sparingly brittle but remains unchanged for 10 revolutions; after 10 revolutions, the wear is more pronounced; this reflects the behaviour of a solid. |
| Example 6 (comparative) | No measurement possible since no film was initially formed: behaviour of an oil. |

It is thus found that there is no decrease in the refractive index after functionalization. The oil keeps its glossy nature, even when functionalized. It is also found that functionalization with ureidopyrimidones leads to films that are more or less tacky, but that do not transfer onto the fingers, unlike the comparative films.

Furthermore, and principally, in the case of the oils functionalized with isophorone (comparative), the films dewet and do not form a uniform deposit. In contrast, the films obtained with the compounds according to the invention do not dewet and are uniform and cohesive. The tribometry results confirm the cohesion properties obtained with the compounds of the invention.

Functionalization with ureidopyrimidones thus leads to materials that are cohesive enough to be able to ensure remanence of the deposit, which, incidentally, is glossy, superior to the remanence of the prior art (isophorone).

In summary: the gloss is maintained, the cohesion of the deposit is improved, and thus its staying power is improved.

Example 8

2-Hexyldecanol Functionalized with Ureidopyrimidone

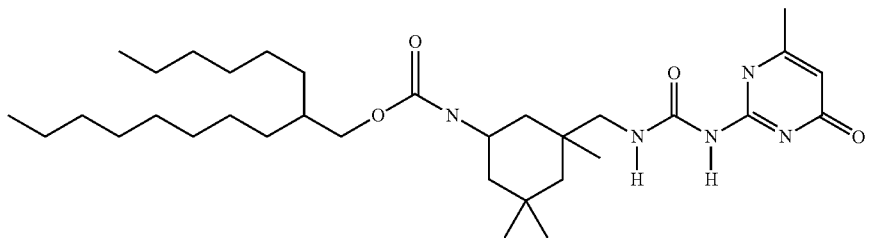 [SMILES: CCCCCCCCC(CCCCCC)COC(=O)NC1CC(C)(C)CC(C)(CNC(=O)Nc2nc(=O)cc(C)[nH]2)C1]

126.4 g of 2-hexyldecanol are heated at 60° C. under reduced pressure for 2 hours to dry them. After 2 hours, the oil is allowed to cool to 20° C. under argon, and is then added slowly, over 5 hours, to a mixture of 116 g of isophorone diisocyanate and 55 mg of DBTL catalyst at 50° C. At the end of the addition, the temperature of the reaction mixture is brought to 110° C., and 90 ml of propylene carbonate and 78.4 g of 6-methylisocytosine are then added, which produces a homogeneous white suspension. Stirring is continued at 110° C. for 2 hours, and the disappearance of the isocyanate is monitored by infrared spectroscopy. The disappearance of the peak at 2250 cm$^{-1}$ is observed. In parallel, disappearance of the amine originating from the isocytosine is monitored by means of an amine assay. At the end of the reaction, 500 g of isododecane are added, at 100° C., and a slightly cloudy pale yellow solution is obtained. 300 ml of ethanol are added and stirring is continued for 2 hours. After filtering through Celite, the reaction mixture is stripped with isododecane at 80° C. in order to remove the alcohol and the propylene carbonate.

Finally, the desired product conveyed in isododecane, in a solids content of 50%, is obtained. The product is especially characterized by HPLC and GPC (structure confirmed).

Example 9

2-Hexyldecanol Functionalized with Ureidopyrimidone

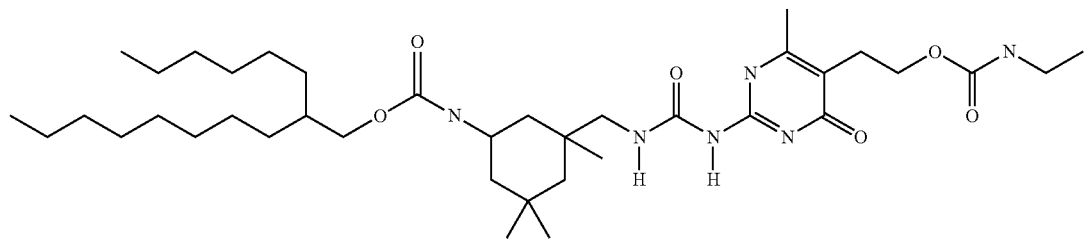

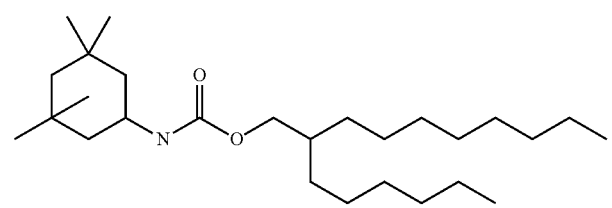

173.1 g of 2-hexyldecanol are heated at 60° C. under reduced pressure for 2 hours to dry them. After 2 hours, the oil is allowed to cool to 50° C. under argon, and is then added slowly, over 5 hours, to a mixture of 158.7 g of isophorone diisocyanate and 77 mg of DBTL catalyst at 50° C. At the end of the addition, the temperature of the reaction mixture is brought to 110° C., and 150 ml of propylene carbonate and 60.3 g of 5-hydroxyethyl-6-methylisocytosine are added, which produces a uniform white suspension. Stirring is continued at 110° C. for 5 hours, and the disappearance of the isocyanate is monitored by infrared spectroscopy. The disappearance of the peak at 2250 cm$^{-1}$ is observed. At the end of the reaction, the temperature of the reaction medium is reduced to 100° C., and 780 g of isododecane are added; a pale yellow cloudy mixture is obtained. 100 ml of ethanol are added and stirring is continued for 2 hours. After filtering through Celite, the reaction mixture is stripped with isododecane at 80° C. in order to remove the alcohol and the propylene carbonate.

Finally, the desired product conveyed in isododecane, in a solids content of 50%, is obtained. The product is especially characterized by HPLC and GPC (structure confirmed).

Example 10

2-Decyltetradecanol Functionalized with Ureidopyrimidone 126 g of 2-decyltetradecanol are heated at 100° C. under reduced pressure for 4 hours to dry them. After 2 hours, the oil is added, over 4 hours, at 50° C. and under argon, to a mixture of 94.7 g of isophorone diisocyanate and of DBTL catalyst (qs). Monitoring by assay of the isocyanate allows the reaction progress to be followed; at half-equivalence, 126 g of propylene carbonate and 53.3 g of 6-methylisocytosine are added. Stirring and heating are continued at 100° C. for 16 hours, and disappearance of the isocyanate is monitored by infrared spectroscopy. The disappearance of the peak at 2250 cm$^{-1}$ is observed. In parallel, disappearance of the amine originating from the isocytosine is monitored by means of an amine assay. At the end of the reaction, the temperature is cooled to 50° C., 100 ml of ethanol are added and stirring is continued for 5 hours. After filtering through Celite and stripping with isododecane, the desired product conveyed in isododecane, at a solids content of 50%, is obtained. The product is especially characterized by GPC and HPLC coupled to mass spectroscopy.

Example 11

A gloss is prepared, comprising (weight %):
36% of compound prepared in Example 1 (solids)
5% of DC Red 7 pigment
qs 100% of isododecane.
After applying to the lips, a very glossy deposit is formed.
Similar glosses are prepared with the compounds of Examples 2, 3, 8, 9 and 10.

Example 12

A gloss is prepared, comprising:
50% of compound prepared in Example 2 (solids)
5% of DC Red 7 pigment
qs 100% of isododecane.

Similar glosses are prepared with the compounds of Examples 1, 3, 8, 9 and 10.

Example 13

A nail varnish is prepared, comprising (weight %):

| | |
|---|---|
| nitrocellulose | 15% |
| polymer of Example 3 (solids) | 9% |
| tributyl acetyl citrate | 5% |
| pigments | 1% |
| hectorite | 1.2% |
| isopropyl alcohol | 8% |
| ethyl acetate, butyl acetate | qs 100% |

Similar nail varnishes are prepared with the compounds of Examples 1, 2, 8, 9 and 10.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more."

The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition comprising, in a cosmetically or dermatologically acceptable medium, a nonpolymeric compound which is a reaction product of:
   an oil comprising a hydroxyl group and/or an amine group, and
   a compound comprising:
   a junction group comprising a reactive function which covalently reacts with the hydroxyl and/or amine group of the oil, and a unit of formula (I) or (II):

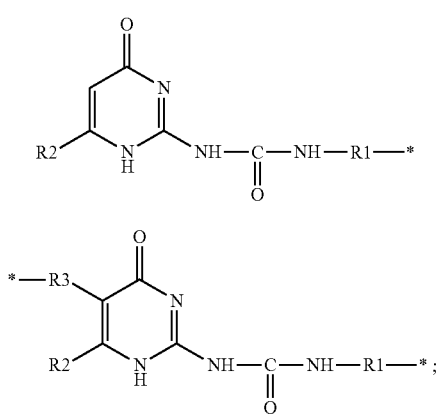

wherein
the junction group is capable of establishing hydrogen bonds with one or more partner junction groups, each junction group pairing involving at least 3 hydrogen bonds,
wherein:
R1 and R3 are each independently (i) a linear or branched $C_1$-$C_{32}$ alkylene group, (ii) a $C_4$-$C_{16}$ cycloalkylene group or (iii) a $C_4$-$C_{16}$ arylene group; each optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 is a hydrogen atom or a linear, branched or cyclic, saturated or unsaturated, optionally aromatic, $C_1$-$C_{32}$ carbon-based radical, which may comprise one or more heteroatoms chosen from O, N, S, F, Si and P, and
wherein the oil is at least one selected from the group consisting of:
(i) a saturated or unsaturated, linear, branched or cyclic fatty alcohol having 6 to 50 carbon atoms and one or more OH; optionally comprising one or more $NH_2$;
(ii) a hydroxylated monocarboxylic acid ester obtained by reacting a monocarboxylic acid having at least one free OH with a monoalcohol or a polyol;
(iii) a partial polyol ester obtained from linear or branched, saturated or unsaturated monoacids containing 6 to 50 carbon atoms and from at least one branched aliphatic and/or alicyclic C32-C38 diol or a polyol selected from the group consisting of propylene glycol, glycerol, neopentyl glycol, trimethylolpropane, trimethylolethane, polyglycerol-2, polyglycerol-3 and polyglycerol-10; erythritol, dipentaerythritol, pentaerythritol, bis(trimethylolpropane), phytanetriol, sucrose, glucose, methylglucose, sorbitol, fructose, xylose, mannitol and glucosamine; and
(iv) a hydrogenated or non-hydrogenated castor oil.

2. The composition according to claim 1, in which, in the junction group, the radical R1 is:
a linear or branched, divalent $C_2$-$C_{12}$ alkylene group;
a divalent $C_4$-$C_{12}$ cycloalkylene or arylene group;
4,4-bisphenylenemethylene;

or of the structures:

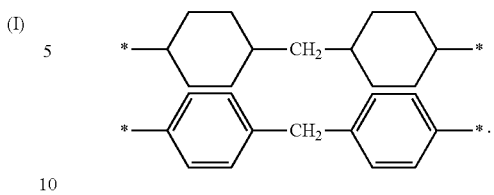

3. The composition according to claim 1, in which, in the junction group, the radical R2 is H or:
a $C_1$-$C_{32}$ alkyl group;
a $C_4$-$C_{12}$ cycloalkyl group;
a $C_4$-$C_{12}$ aryl group;
a ($C_4$-$C_{12}$)aryl($C_1$-$C_{18}$)alkyl group;
a $C_1$-$C_4$ alkoxy group;
an arylalkoxy group;
a $C_4$-$C_{12}$ heterocycle;
or a combination of these radicals, which may be optionally substituted with an amino, ester and/or hydroxyl function.

4. The composition according to claim 1, in which, in the junction group, the radical R3 is a divalent radical —R'3-O—C(O)—NH—R'4- in which R'3 and R'4, which may be identical or different, are a divalent carbon-based radical chosen from a linear or branched $C_1$-$C_{32}$ alkyl group, a $C_4$-$C_{16}$ cycloalkyl group and a $C_4$-$C_{16}$ aryl group; or a mixture thereof.

5. The composition according to claim 1, in which, in the junction group,
(a) in formula (I), the following apply:
R1=-isophorone- and R2=methyl,
R1=—($CH_2$)$_6$— and R2=methyl,
R1=—($CH_2$)$_6$— and R2=isopropyl, or
R1=4,4'-methylenebiscyclohexylene and R2=methyl,
or
(b) in formula (II), R1 is an -isophorone- radical, R2=methyl and R3=—($CH_2$)$_2$OCO—NH-isophorone-.

6. The composition according to claim 1, in which the junction group has the formula:

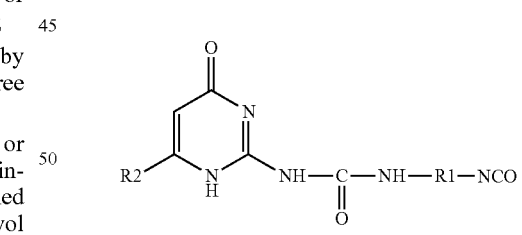

or the formula:

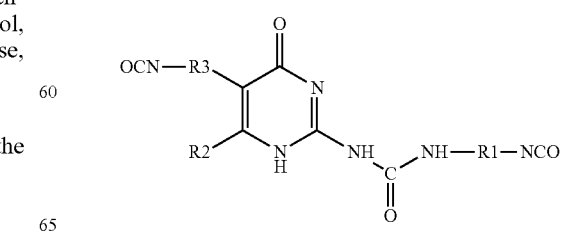

in which

R1 and R3, which may be identical or different, are a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups; and R2 is a hydrogen atom or a linear, branched or cyclic, saturated or unsaturated, optionally aromatic, $C_1$-$C_{32}$ carbon-based radical, which may comprise one or more heteroatoms chosen from O, N, S, F, Si and P.

7. The composition according to claim 1, wherein the junction group is at least one selected from group consisting of:

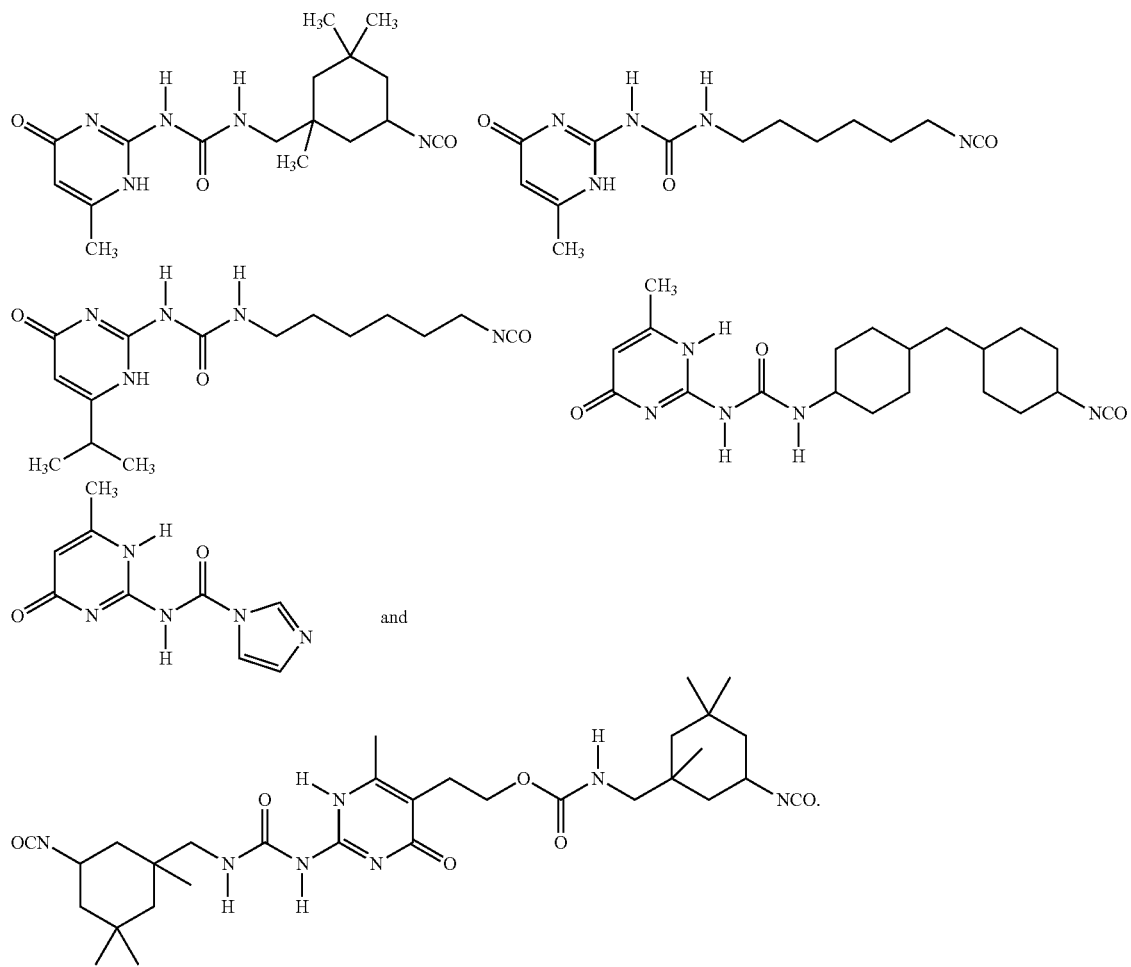

and

8. The composition according to claim 1, wherein the nonpolymeric compound is at least one selected from the group consisting of:

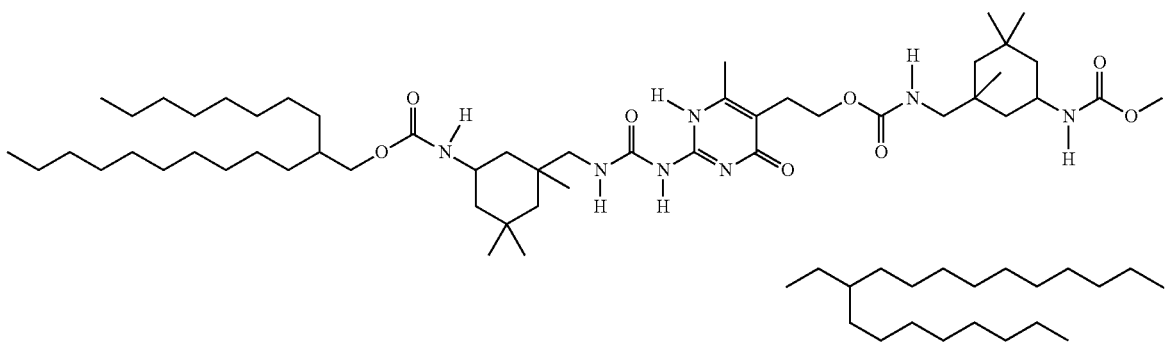

-continued
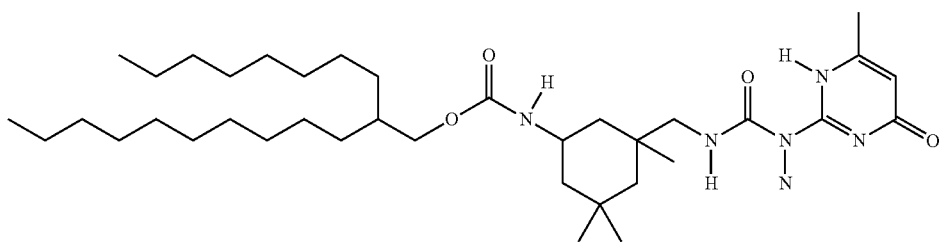
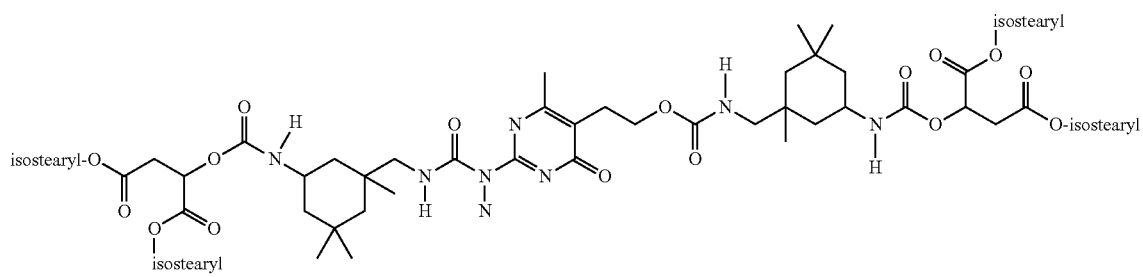
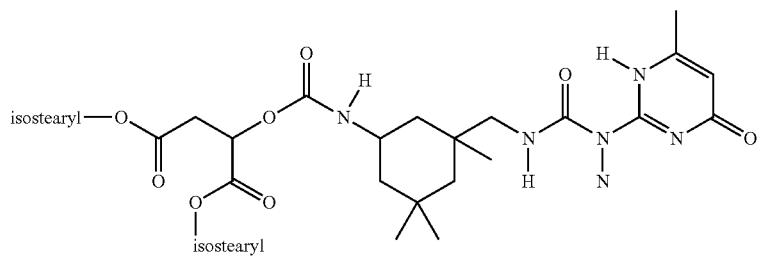
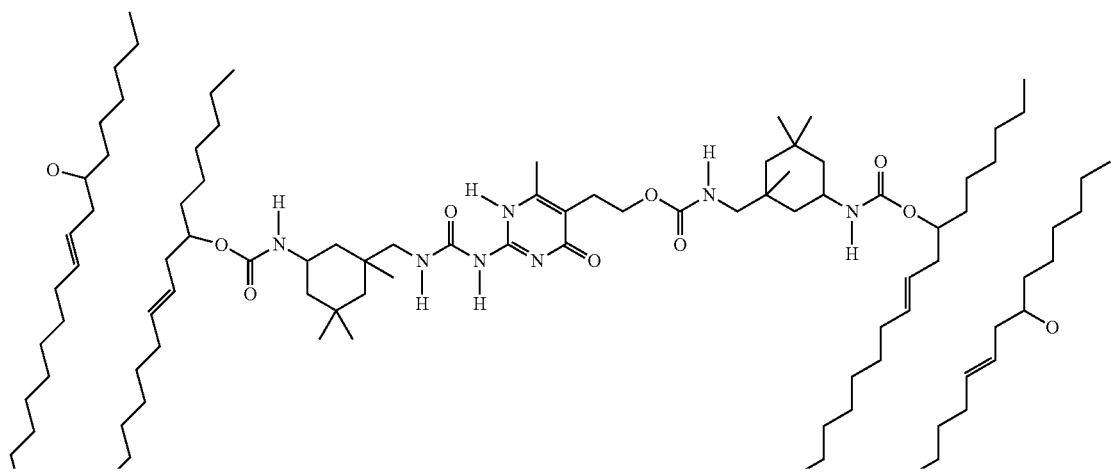

43 44
-continued
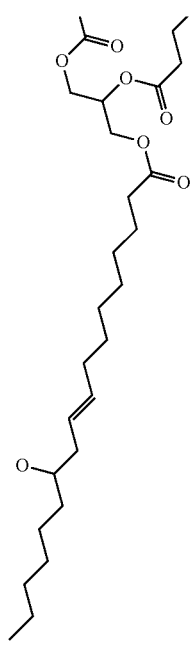
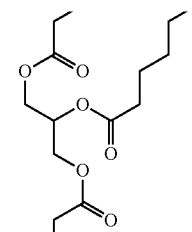
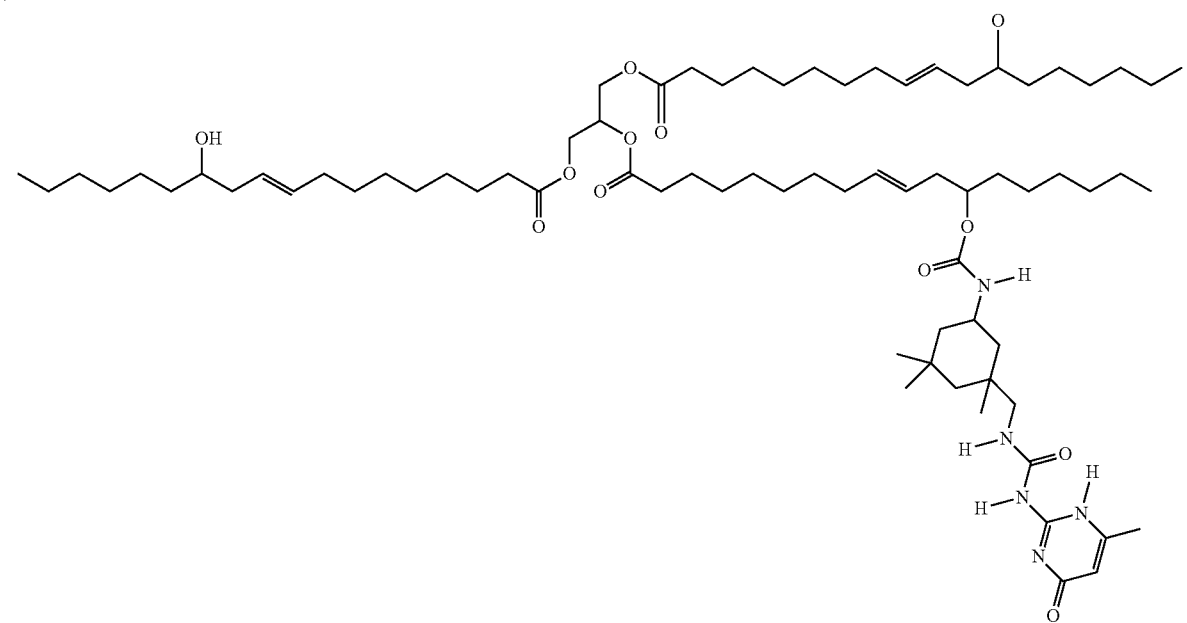
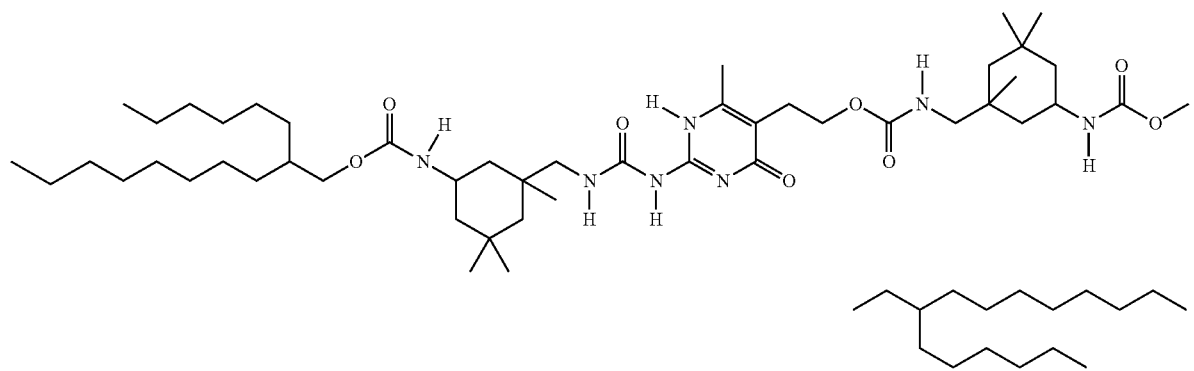

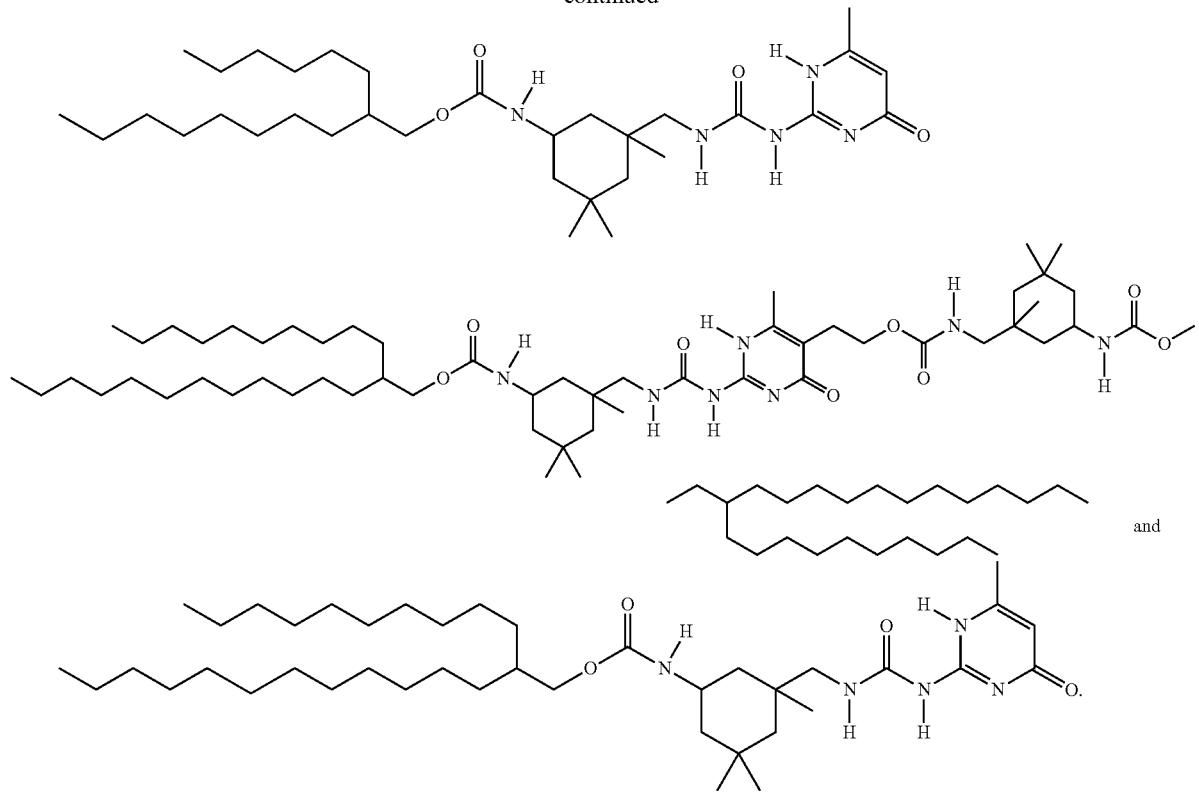

9. The composition according to claim 1, in which the number-average molecular mass (Mn) of the nonpolymeric compound is between 180 and 8000 g/mol.

10. The composition according to claim 1, in which the amount of the nonpolymeric compound present in the composition is between 5% and 80% by weight relative to the weight of the cosmetic or dermatological composition.

11. The composition according to claim 1, which is in the form of a care and/or makeup composition for bodily or facial skin, the lips, the eyelashes, the eyebrows or the nails; an antisun or self-tanning product.

12. A process for treating a keratin material, comprising application to the keratin material of a composition according to claim 1.

13. The composition according to claim 1, wherein the the hydroxylated monocarboxylic acid ester is obtained by reacting a carboxylic acid selected from the group consisting of monohydroxylated acids containing 4 to 28 carbon atoms and lactic acid, with a linear or branched C3-C50 alcohol.

14. The composition according to claim 1, wherein the the hydroxylated monocarboxylic acid ester is obtained by reacting a carboxylic acid selected from the group consisting of hydroxystearic acid, ricinoleic acid, malic acid, lactic acid and citric acid; and mixtures thereof, with an C3-C50 alcohol selected from the group consisting of 2-ethylhexanol, octanol and isostearyl alcohol, and mixtures thereof.

15. The composition according to claim 1, wherein the oil is (ii) the hydroxylated monocarboxylic acid ester selected from the group consisting of a C4-40 alkyl malate, a C4-40 alkyl lactate, a C4-40 alkyl citrate, and an ester of 12-hydroxystearic acid.

16. The composition according to claim 15, wherein the oil is (ii) a C4-40 alkyl malate selected from the group consisting of bis(2-ethylhexyl) malate, diisostearyl malate and bis(2-octyldodecyl) malate.

17. The composition according to claim 15, wherein the oil is (ii) a C4-40 alkyl lactate selected from the group consisting of 2-ethylhexyl lactate, diisostearyl lactate, isostearyl lactate, isononyl lactate and 2-octyldodecyl lactate.

18. The composition according to claim 15, wherein the oil is (ii) a C4-40 alkyl citrate selected from the group consisting of triisostearyl citrate, triisocetyl citrate and triisoarachidyl citrate.

19. The composition according to claim 15, wherein the oil is (ii) an ester of 12-hydroxystearic acid selected from the group consisting of octyl hydroxystearate and 2-octyldodecyl hydroxystearate.

20. The composition according to claim 1, wherein the oil is at least one saturated or unsaturated, linear or branched C8-C28 monoalcohol.

21. The composition according to claim 20, wherein the oil is at least one monoalcohol selected from the group consisting of isostearyl alcohol, oleyl alcohol, isopalmitoyl alcohol, 2-butyloctanol, 2-hexyldecanol, 2-octyldecanol, 2-octyldodecanol, 2-octyltetradecanol, 2-decyltetradecanol and 2-dodecylhexadecanol.

22. The composition according to claim 1, wherein the oil is (iii) at least one partial polyol ester selected from the group consisting of a pentaerythritol partial ester, a dipentaerythritol ester, a trimethylolpropane ester, a bis(trimethylolpropane) ester, a glycerol ester, a propylene glycol monoester and a diol dimer monoester.

23. The composition according to claim 22, wherein the oil is (iii) at least one pentaerythritol partial ester selected from the group consisting of pentaerythrityl adipate, pentaerythrityl caprate, pentaerythrityl succinate, pentaerythrityl tetraisononanoate, pentaerythrityl triisononanoate, pentaerythrityl tetraisostearate, pentaerythrityl triisostearate, pentaerythrityl 2-(tetradecyl)tetradecanoate, pentaerythrityl (tetraethyl)hexanoate and pentaerythrityl (tetraoctyl)dodecanoate.

24. The composition according to claim 22, wherein the oil is (iii) at least one dipentaerythritol ester selected from the group consisting of dipentaerythrityl pentaisononanoate, dipentaerythrityl pentaisostearate, dipentaerythrityl tetraisostearate and dipentaerythrityl tris(polyhydroxystearate).

25. The composition according to claim 22, wherein the oil is (iii) at least one trimethylolpropane ester selected from the group consisting of trimethylolpropane monoesters and diesters selected from trimethylolpropane monoisostearate, trimethylolpropane diisostearate, trimethylolpropane mono-2-ethylhexanoate and trimethylolpropane bis(2-ethylhexanoate).

26. The composition according to claim 22, wherein the oil is (iii) at least one bis(trimethylolpropane ester selected from the group consisting of bis(trimethylolpropane) diisostearate, bis(trimethylolpropane) triisostearate and bis(trimethylolpropane) triethylhexanoate.

27. The composition according to claim 22, wherein the oil is (iii) at least one glycerol ester selected from the group consisting of
- glyceryl diisostearate, glyceryl diisononanoate,
- a polyglycerol-2 monoesters, diesters and triesters with isostearic acid, 2-ethylhexanoic acid and/or isononanoic acid, polyglyceryl-2 isostearate; polyglyceryl-2 diisostearate; polyglyceryl-2 triisostearate; polyglyceryl-2 nonaisostearate; polyglyceryl-2 nonanoate;
- polyglycerol-3 monoesters, diesters, triesters or tetraesters; optionally with either isostearic acid, 2-ethylhexanoic acid and/or isononanoic acid; and especially polyglyceryl-3 isostearate; polyglyceryl-3 diisostearate; polyglyceryl-3 triisostearate; polyglyceryl-3 nonaisostearate; polyglyceryl-3 nonanoate;
- polyglycerol-10 partial esters and in particular polyglyceryl-10 nonaisostearate; polyglyceryl-10 nonanoate; polyglyceryl-10 isostearate; polyglyceryl-10 diisostearate; and polyglyceryl-10 triisostearate.

28. The composition according to claim 22, wherein the oil is (iii) at least one propylene glycol monoester selected from the group consisting of propylene glycol monoisostearate, propylene glycol neopentanoate and propylene glycol monooctanoate.

29. The composition according to claim 22, wherein the oil is (iii) at least one diol dimer monoester selected from the group consisting of isostearyl dimer dilinoleate and octyldodecyl dimer dilinoleate.

30. The composition of claim 1, wherein of the oil reacts chemically with the isocyanate or imidazole groups borne by the junction group.

* * * * *

UNITED STATES PATENT AND TRADEMARK OFFICE
CERTIFICATE OF CORRECTION

PATENT NO. : 9,504,856 B2  
APPLICATION NO. : 12/495875  
DATED : November 29, 2016  
INVENTOR(S) : Sandrine Chodorowski-Kimmes et al.

Page 1 of 1

It is certified that error appears in the above-identified patent and that said Letters Patent is hereby corrected as shown below:

In the Claims

Column 37, Line 55 (Claim 1), "polyglyccrol-3" should read -- polyglycerol-3 --

Column 45, Line 49 (Claim 13), "the the" should read -- the --

Column 45, Line 54 (Claim 14), "the the" should read -- the --

Signed and Sealed this  
First Day of May, 2018

Andrei Iancu  
*Director of the United States Patent and Trademark Office*